(12) United States Patent
Wolfenden et al.

(10) Patent No.: US 11,395,479 B2
(45) Date of Patent: Jul. 26, 2022

(54) METHOD TO REDUCE MICROBIAL BLOOM IN POULTRY HATCHERY

(71) Applicants: Novozymes A/S, Bagsvaerd (DK); Board of Trustees of the University of Arkansas, Little Rock, AR (US)

(72) Inventors: Ross Wolfenden, Fayetteville, AR (US); Jacob Lum, Fayetteville, AR (US); Billy Hargis, Fayetteville, AR (US); Lisa Bielke, Fayetteville, AR (US); Lucas Graham, Fayetteville, AR (US)

(73) Assignees: Novozymes A/S, Bagsvaerd (DK); Board of Trustees of the University of Arkansas, Little Rock, AR (US)

( * ) Notice: Subject to any disclaimer, the term of this patent is extended or adjusted under 35 U.S.C. 154(b) by 830 days.

(21) Appl. No.: 16/069,446

(22) PCT Filed: Jan. 25, 2017

(86) PCT No.: PCT/US2017/014888
§ 371 (c)(1),
(2) Date: Jul. 11, 2018

(87) PCT Pub. No.: WO2017/132230
PCT Pub. Date: Aug. 3, 2017

(65) Prior Publication Data
US 2019/0029230 A1 Jan. 31, 2019

Related U.S. Application Data

(60) Provisional application No. 62/286,759, filed on Jan. 25, 2016.

(51) Int. Cl.
| | | |
|---|---|---|
| A01K 45/00 | (2006.01) |
| A61K 35/744 | (2015.01) |
| C12N 1/20 | (2006.01) |
| A61K 35/742 | (2015.01) |
| A61K 35/745 | (2015.01) |
| A61P 31/04 | (2006.01) |
| A01K 41/00 | (2006.01) |
| A61K 35/741 | (2015.01) |
| A61K 35/00 | (2006.01) |

(52) U.S. Cl.
CPC ............ *A01K 45/007* (2013.01); *A01K 41/00* (2013.01); *A61K 35/741* (2013.01); *A61K 35/742* (2013.01); *A61K 35/744* (2013.01); *A61K 35/745* (2013.01); *A61P 31/04* (2018.01); *C12N 1/20* (2013.01); *A61K 2035/115* (2013.01)

(58) Field of Classification Search
None
See application file for complete search history.

(56) References Cited

U.S. PATENT DOCUMENTS

| | | |
|---|---|---|
| 5,868,998 A | 2/1999 | Larose |
| 2002/0018770 A1 | 2/2002 | Maruta |
| 2010/0092428 A1 | 4/2010 | Schmidt et al. |
| 2010/0143316 A1 | 6/2010 | Hsieh |
| 2010/0196323 A1 | 8/2010 | Plail |
| 2011/0076745 A1 | 3/2011 | Yuki |
| 2014/0199281 A1* | 7/2014 | Henn .................. A61K 9/4891 424/93.46 |
| 2015/0037307 A1 | 2/2015 | Bralkowski et al. |

FOREIGN PATENT DOCUMENTS

| | | |
|---|---|---|
| KR | 2015 0117184 | 10/2015 |
| WO | 99/28441 A1 | 12/1997 |
| WO | 2008/073406 A2 | 6/2008 |
| WO | 2012/009712 A2 | 1/2012 |
| WO | 2012/110777 A2 | 8/2012 |
| WO | 2014/108937 A1 | 7/2014 |
| WO | 2016/011511 A1 | 1/2016 |

OTHER PUBLICATIONS

From et al, 2005, Appl Environ Microbiol 71(3), 1178-1183.
Hernandez et al, 1998, Journal of clinical microbiology 36(7), 2138-2139.
Little et al, 1999, Microbes and infection 2, 131-139.
Ghareeb et al., Poultry Science, vol. 91, No. 8, pp. 1825-1832 (2012).
Kim et al., WPI Accession No. AN 2015-66045P (2015).
O'Dea et al., Poultry Science, vol. 85, No. 10, pp. 1855-1863 (2006).
Promsopone et al., Journal of Food Protection, vol. 61, No. 2, pp. 176-180 (1998).
Wolfenden et al., Poultry Science, vol. 90, No. 11, pp. 2627-2631 (2011).
Cao et al, 2013, Poultry Science, vol. 92, No. 11, pp. 2949-2955.

* cited by examiner

Primary Examiner — Brian Gangle
(74) Attorney, Agent, or Firm — Adam Rucker

(57) ABSTRACT

Spore forming bacteria and Lactic Acid Bacteria for application in poultry hatcher cabinets to alter the bacterial bloom towards a more beneficial microbiota, positively affecting performance parameters such as mortality, body weight gain and feed conversion ratio throughout production.

20 Claims, 9 Drawing Sheets

Specification includes a Sequence Listing.

Figure 1. Non-selective bacterial recovery after treatment with *Bacillus* spores and aqueous Lactic Acid Bacteria Arrows indicate application times. DBS, dry *Bacillus* spray. WBS, wet *Bacillus* spray.

METHOD TO REDUCE MICROBIAL BLOOM IN POULTRY HATCHERY

CROSS-REFERENCE TO RELATED APPLICATIONS

This application is a 35 U.S.C. 371 national application of international application no. PCT/US2017/014888 filed Jan. 25, 2017, which claims priority or the benefit under 35 U.S.C. 119 of U.S. provisional application no. 62/286,759 filed Jan. 25, 2016. The content of each application is fully incorporated herein by reference.

REFERENCE TO A DEPOSIT OF BIOLOGICAL MATERIAL

This application contains a reference to a deposit of biological material, which deposit is incorporated herein by reference. For complete information see Example 1.

REFERENCE TO SEQUENCE LISTING

This application contains a Sequence Listing in computer readable form. The computer readable form is incorporated herein by reference.
Index to Sequence Listing:
SEQ ID NO: 1 is 16S rDNA of *Pediococcus acidilactici* FM18 deposited as NRRL B-50964.
SEQ ID NO: 2 is 16S rDNA of *Pediococcus acidilactici* TY036 deposited as NRRL B-50959.
SEQ ID NO: 3 is 16S rDNA of *Enterococcus faecium* MFF109 deposited as NRRL B-50960.
SEQ ID NO: 4 is 16S rDNA of *Bacillus amyloliquefaciens* AM0904 deposited as NRRL B-50914.
SEQ ID NO: 5 is 16S rDNA of *Bacillus amyloliquefaciens* NP122 deposited as NRRL B-50910.
SEQ ID NO: 6 is 16S rDNA of *Bacillus amyloliquefaciens* B2 deposited as NRRL B-50908.

FIELD OF THE INVENTION

The invention relates to spore forming bacteria and/or Lactic Acid Bacteria for application in poultry hatcher cabinets to alter the microbial bloom towards a more beneficial microbiota, positively affecting performance parameters such as mortality, body weight gain and/or Feed Conversion Ratio throughout poultry production.

BACKGROUND OF THE INVENTION

Modern poultry hatcheries have expanded in size and scale due to increased consumer demand. An increase in hatchery output necessitates an increase in related operations, such as movement of personnel and vehicles and near-continuous use of hatchery facilities. To ensure the production of healthy disease-free chicks, maximum sanitary standards must be observed, especially with respect to eggs and any equipment that will come into contact with eggs. One area of the hatchery that requires special care is the hatching cabinets, where the chicks will hatch and be exposed to the first bacteria that colonize the naive gut.

Often the bacteria present in a hatching cabinet may not be beneficial to the newborn chicks and may even be harmful, such as *Salmonella, E. coli, Pseudomonas, Streptococcus, Staphylococcus, Enterococcus,* among others. The warm, humid climate of the hatching cabinets is conducive to the growth of these organisms so reducing contamination and preventing "microbial blooms" is of the utmost importance. Additionally, the Gastro-Intestinal Tract (GIT) of poultry is dependent on healthy gut bacteria to stimulate intestinal and immune development. The sooner the neonatal poultry are exposed to these "good" bacteria, the less likely they are to be colonized by pathogenic bacteria and the sooner their GIT will begin to develop.

Traditionally hatchery sanitation has been accomplished by the use of antimicrobial chemicals, primarily fumigated formaldehyde to reduce the pathogens from the hatcher. Upon arrival at the hatchery, eggs are sometimes sanitized to remove microbes transferred from the hen and fecal material. This does not remove all bacteria, which will continue to grow in the warm, humid environment of the setters and may bloom after transfer into the hatching cabinets. This can also reduce hatchability of the eggs. It is common to fumigate the hatching cabinets with formaldehyde to prevent this bloom, though the formaldehyde may cause some ill effects to the chicks itself, as it is a known irritant, and is a safety hazard to hatchery personnel. High concentrations of formaldehyde can cause irritation of the mucous membranes in both birds and humans and trigger asthma-like symptoms and is carcinogenic in humans. Numerous countries have moved to ban or drastically lower the short-term-exposure-limit for formaldehyde, so various alternatives have been tested over the past several years. Additionally handling of formaldehyde requires extensive safety training and specialized equipment to safely apply.

Several chemical alternatives to formaldehyde have been proposed, such as quaternary ammonium and glutaraldehyde. Though safer and non-carcinogenic, glutaraldehyde is still considered an irritant and is toxic and therefore the maximum exposure limit is set at 0.05 ppm. While safer, these chemical alternatives have not been as effective at controlling the bacterial "bloom" within the hatchers.

With growing thought for employee safety and consumer push for removing chemicals from the food chain, there has been growing research into biological solutions for sanitation and microbial control in the agricultural industry. Formaldehyde and other chemical disinfectants also do not address the need for exposure to helpful, commensal bacteria.

To accomplish this, probiotic bacterial formulations have been applied post hatch. These have generally been applied either at the hatchery during processing of the chicks or soon after placement at the poultry farm.

Promsopone et al. (*J. Food Protection* 61(2): 176-180 (1998)) describe the use of *Lactobacillus acidophilus, Streptococcus faecium,* and *S. typhimurium*-specific antibodies for reducing *S. typhimurium* in broiler chicks.

However, the time from hatch to first exposure to these probiotic bacteria can range up to 48 hours post hatch depending on actual hatch time of a given chick and when the probiotic is applied post hatch. Since broiler chickens only live an average of 42 days, 48 hours is a significant period of time before they are provided with beneficial microorganisms. Additionally, as pathogenic bacteria are relatively more common in the hatcher and hatchery environment, chicks are more likely to get exposure to pathogens before commensals.

There is thus a need for a formulation such as, e.g., a probiotic formulation, which controls the bacterial bloom in the hatchery without having the drawbacks of formaldehyde and other chemical disinfectants.

SUMMARY OF THE INVENTION

The invention relates to a method for improving one or more performance parameter(s) of poultry comprising the step of administering one or more probiotic(s) in the poultry hatcher cabinet.

The invention further relates to composition capable of improving one or more performance parameter(s) of poultry after administering of said composition in the poultry hatcher cabinet. In one preferred embodiment, the composition includes at least one lactic acid bacteria (such as *Pediococcus acidilactici* FM18 deposited as NRRL Deposit Number B-50964, *Pediococcus acidilactici* TY036 deposited as NRRL Deposit Number B-50959, or *Enterococcus faecium* MFF109 deposited as NRRL Deposit Number B-50960) and/or at least one *Bacillus* (such as *Bacillus amyloliquefaciens* AM0904 deposited as NRRL Deposit Number B-50914, *Bacillus amyloliquefaciens* NP122 deposited as NRRL Deposit Number B-50910, or *Bacillus amyloliquefaciens* B2 deposited as NRRL Deposit Number B-50908). The bacterial isolates have been deposited with the Agricultural Research Service Culture Collection (NRRL), 1815 North University Street, Peoria, Ill. 61604, U.S.A., under the above-identified accession numbers.

BRIEF DESCRIPTION OF DRAWINGS

FIG. 1 illustrates amount of general bacteria present in hatcher post administration of bacterial formulation in experiment 1.

DEFINITIONS

Figure 2:
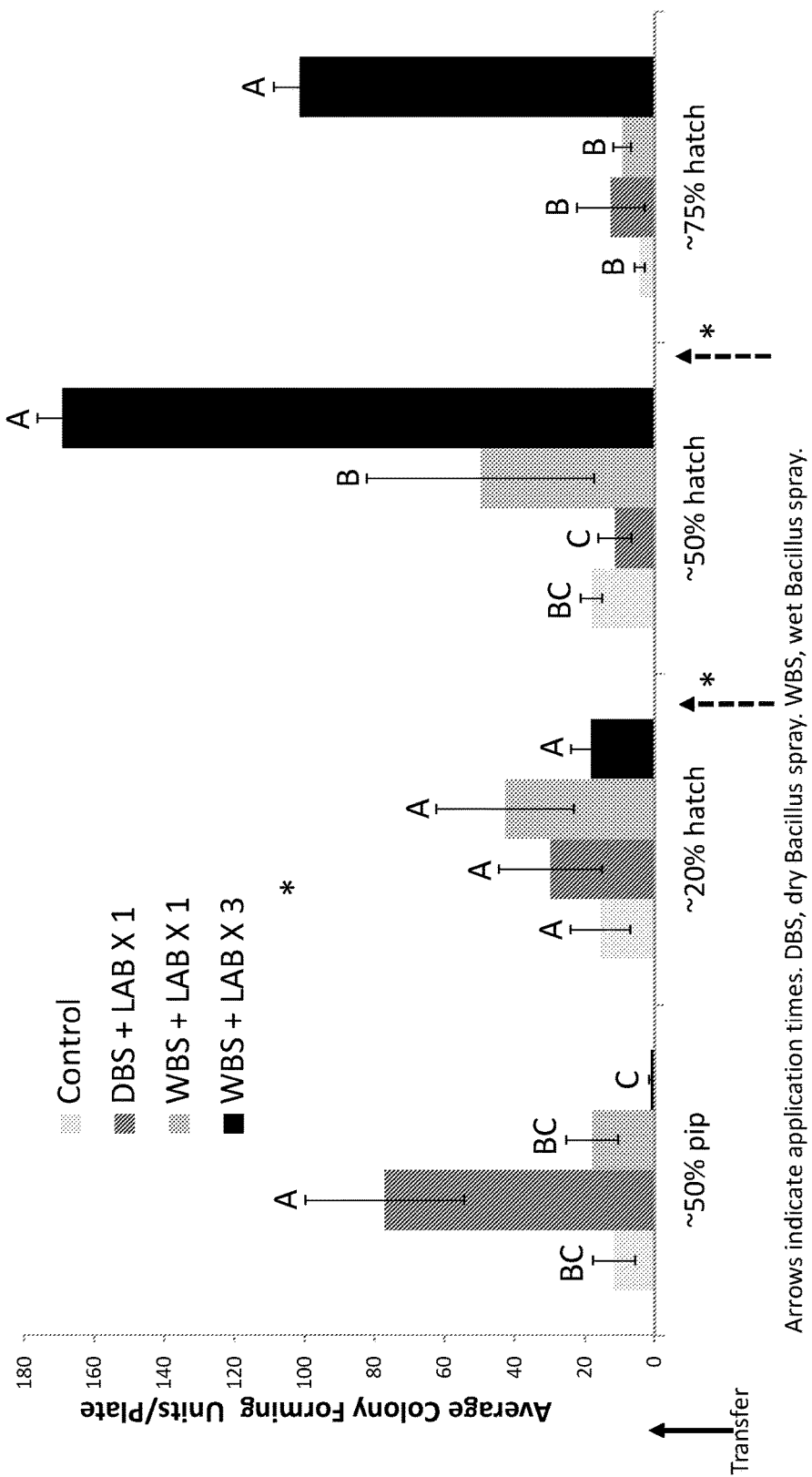
FIG. 2 illustrates amount of lactic acid bacteria present in hatcher post administration of bacterial formulation in experiment 1.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

The term "consisting of" means including, and limited to, whatever follows the phrase "consisting of." Thus, the phrase "consisting of" indicates that the listed elements are required or mandatory, and that no other elements may be present. The term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "administering," or "administer" include providing a probiotic formulation of the disclosure to an animal preferably by oral administration.

A "decreased" or "reduced" amount is typically a "statistically significant" amount, and may include a decrease that is 1, 2, 3, 4, 5, 6, 7, 8, 9, 10, 15, 20, 30, 40, 50, 100, 200, 250, 500, 1000 or more times less, including all integers and decimal points in between and above 1 (e.g., 1.1, 1.2, 1.3, 1.4, 1.5, 1.6, 1.7, 1.8, 1.9), than the amount produced by an animal in the absence of a probiotic formulation. A decrease may include a decrease that is at least one log ($Log_{10}$) or more less than the amount produced by an animal in the absence of a probiotic formulation. A decreased or reduced amount may include a decrease that is at least about 5 fold, 10 fold, 15 fold, 20 fold, 25 fold or 30 fold less than the amount produced by an animal in the absence of a probiotic formulation.

A "decrease" in a response may be "statistically significant" as compared to the response produced by an animal in the absence of a probiotic formulation, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

An "increased" amount is typically a "statistically significant" amount, and may include an increase that is 1, 2, 3, 4, 5, 6, 7, 8, 9, 10, 15, 20, 30, 40, 50, 100, 200, 250, 500, 1000 or more times more, including all integers and decimal points in between and above 1 (e.g., 1.1, 1.2, 1.3, 1.4, 1.5, 1.6, 1.7, 1.8, 1.9), than the amount produced by an animal in the absence of a probiotic formulation. An increase may include an increase that is at least one log ($Log_{10}$) or more less than the amount produced by an animal in the absence of a probiotic formulation. An increased amount may include an increase that is at least about 5 fold, 10 fold, 15 fold, 20 fold, 25 fold or 30 fold more than the amount produced by an animal in the absence of a probiotic formulation.

An "increase" in a response may be "statistically significant" as compared to the response produced by an animal in the absence of a probiotic formulation, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase, including all integers in between.

The term "isolated" refers to a material that is substantially or essentially free from components that normally accompany it in its native state. For example, an isolated bacterial isolate may refer to a bacterial isolate that has been purified or removed from naturally or non-naturally occurring components that are present in its naturally occurring environment.

The term "modify" includes to "decrease" one or more quantifiable parameters or indications, optionally by a defined and/or statistically significant amount. By "decrease" or "decreasing," "reduce" or "reducing," refers generally to the ability of a probiotic formulation to produce a lesser physiological response in an animal relative to the response caused by a control formulation. Relevant physical responses will be apparent to persons skilled in the art. A "decreased" or "reduced" amount is typically a "statistically significant" amount, and may include a decrease that is 1, 2, 3, 4, 5, 6, 7, 8, 9, 10, 15, 20, 30, 40, 50 or more times less (e.g., 100, 500, 1000 times), including all integers and decimal points in between and above 1 (e.g., 1.1, 1.2, 1.3, 1.4, 1.5, 1.6, 1.7, 1.8, 1.9), the amount produced by an animal in the absence of a probiotic formulation. A decrease may include a decrease that is at least one log ($Log_{10}$) or more less than the amount produced by an animal in the absence of a probiotic formulation. A decreased or reduced amount may include a decrease that is at least about 5 fold, 10 fold, 15 fold, 20 fold, 25 fold or 30 fold less than the amount produced by an animal in the absence of a probiotic formulation.

As used herein, the terms "quantifying," "quantification" or other related words refer to determining the quantity, mass, or concentration in a unit volume, of a parameter or indication.

As used herein, the term "poultry" refers to domesticated birds. Poultry includes wildfowl, waterfowl, and game birds. Examples of poultry include, but are not limited to, chicken, broilers, layers, bantams, turkey, duck, geese, guinea fowl, peafowl, quail, dove, pigeon (squab), and pheasant, preferably chickens, broilers, layers and turkeys.

Mortality is defined as the percentage of birds which die or are culled before harvesting. Decreased mortality is a sign of good flock health and low incidence of disease.

Body weight/body weight gain means that the growth rate is increased when the overall health of the animal is improved (less resources spent on stress or disease), the GIT is working more optimally, more nutrients are made available to the animal, and/or feed intake increases.

Feed conversion ratio is the metric for conversion of feed to body weight (Feed intake/body weight). Improvements in feed conversion are attributed to improved absorption of nutrients by the animal. This can mean that the animal is better able to absorb nutrients because of 1) a change in absorptive capacity by the animal 2) more available nutrients in the GIT of the animal. With this metric, a lower number/ration is better than a higher number.

"Hatch" means the breaking of the egg shell whereby a chick comes out of the egg. 10% hatch thus means that 10% of the eggs have broken shells whereby chicken have emerged, 20% hatch means 20% of the eggs have broken shells whereby chicken have emerged, etc.

"Pip" means an egg in which the chick has broken the shell in an attempt to hatch. Sometimes chicks die shortly after piping the shell. 10% pip thus means that 10% of the eggs have broken shells from chicks' piping, 20% pip means 20% of the eggs have broken shells from chicks' piping, etc. Hatcher cabinet is a machine used to maintain proper conditions for setting avian eggs.

The term "probiotic" is herein used for live microorganisms for administration to humans or animals for obtaining associated benefits for humans and animals.

The terms "bacterial bloom" and "microbial bloom" are used interchangeably herein and are understood as an increase in the level of pathogenic bacteria such as a rapid increase in the level of pathogenic bacteria, e.g., due to a warm, humid environment.

Coliform bacteria are known to the person skilled in the art and are rod-shaped Gram-negative non-spore forming and motile or non-motile bacteria which can ferment lactose with the production of acid and gas when incubated at 35-37° C. Their presence is used to indicate that other pathogenic organisms of fecal origin may be present. Examples of coliform bacteria include but are not limited to bacteria of the genera: *Citrobacter, Enterobacter, Hafnia, Klebsiella, Salmonella,* and *Escherichia*.

DETAILED DESCRIPTION OF THE INVENTION

Method for Improving Performance Parameter(s) of Poultry

In one aspect the invention relates to a method for improving one or more performance parameter(s) of poultry comprising the step of administering one or more probiotic(s) in the poultry hatcher cabinet.

The administering is in a preferred embodiment performed by spraying the one or more probiotic(s) into the poultry hatcher cabinet. The ventilation system will preferably ensure a good distribution in the poultry hatcher cabinet. In an even more preferred embodiment the one or more probiotic(s) is a powder formulation such as a dry powder formulation. The dry powder formulation will ensure a good distribution in the poultry hatcher cabinet. Application of the one or more probiotic(s) is preferably accomplished by a dry spray directly into the hatcher cabinet and circulation of the probiotic(s) by the ventilation system in the cabinet. One embodiment relates to dry spray delivering, e.g., by a pneumatic system. The probiotic(s) are preferably on spore form.

In a preferred embodiment of the method the one or more probiotic(s) comprises one or more *Bacillus* strains, e.g., in spore form. In another preferred embodiment the one or more probiotic(s) comprises one or more lactic acid bacteria strains, e.g., in spore form. In a specific embodiment the one or more probiotic(s) comprises one or more *Bacillus* strains (e.g., in spore form) and one or more lactic acid bacteria strains (e.g., in spore form).

The inventor has thus found that one or more *Bacillus* strains and/or one or more lactic acid bacteria strains when provided as a probiotic has a positive effect on the bacterial bloom towards a more beneficial microbiota and/or performance parameters of the poultry. The inventor further surprisingly found that the one or more *Bacillus* strains may be combined with the one or more lactic acid bacteria strains in one probiotic having a positive effect on the bacterial bloom towards a more beneficial microbiota and/or performance parameters of the poultry.

In a specific embodiment of the method the one or more probiotic(s) comprises one or more lactic acid bacteria selected from the group consisting of i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.

The method also relates to an embodiment wherein the one or more probiotic(s) comprises one or more *Bacillus* selected from the group consisting of i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof, ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.

Another embodiment of the method relates to one or more probiotic(s) comprising one or more lactic acid bacteria selected from the group consisting of i) *Pediococcus acidilactici* FM18 deposited as NRRL Deposit Number B-50964, ii) *Pediococcus acidilactici* TY036 deposited as NRRL Deposit Number B-50959, and iii) *Enterococcus faecium* MFF109 deposited as NRRL Deposit Number B-50960.

The method according to the present invention also relates to an embodiment wherein the one or more probiotic(s) comprises one or more *Bacillus* selected from the group consisting of i) *Bacillus amyloliquefaciens* AM0904 deposited as NRRL Deposit Number B-50914, ii) *Bacillus amyloliquefaciens* NP122 deposited as NRRL Deposit Number B-50910, and iii) *Bacillus amyloliquefaciens* B2 deposited as NRRL Deposit Number B-50908.

In a specific embodiment the method relates to one or more probiotic(s) comprising one or more lactic acid bacteria selected from the group consisting of i) *Pediococcus acidilactici* FM18 deposited as NRRL Deposit Number B-50964, ii) *Pediococcus acidilactici* TY036 deposited as NRRL Deposit Number B-50959, and iii) *Enterococcus faecium* MFF109 deposited as NRRL Deposit Number B-50960; and one or more probiotic(s) comprising one or more *Bacillus* selected from the group consisting of i) *Bacillus amyloliquefaciens* AM0904 deposited as NRRL Deposit Number B-50914, ii) *Bacillus amyloliquefaciens* NP122 deposited as NRRL Deposit Number B-50910, and iii) *Bacillus amyloliquefaciens* B2 deposited as NRRL Deposit Number B-50908.

In another specific embodiment the method relates to one or more probiotic(s) comprising one or more lactic acid bacteria selected from the group consisting of i) *Pediococcus acidilactici* FM18 deposited as NRRL Deposit Number B-50964, and ii) *Pediococcus acidilactici* TY036 deposited as NRRL Deposit Number B-50959;

and one or more probiotic(s) comprising one or more *Bacillus* selected from the group consisting of i) *Bacillus amyloliquefaciens* AM0904 deposited as NRRL Deposit Number B-50914, ii) *Bacillus amyloliquefaciens* NP122 deposited as NRRL Deposit Number B-50910, and iii) *Bacillus amyloliquefaciens* B2 deposited as NRRL Deposit Number B-50908.

In another embodiment of the method the one or more probiotic(s) comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

In one embodiment the method described above results in improvement of one or more performance parameter(s) selected from the group consisting of body weight gain, growth rate, feed conversion rate and overall health or any combination thereof. The method can further result in an increase in healthy gut bacteria that stimulate intestinal and/or immune development in the poultry. In one embodiment the method results in an increase in the level of lactic acid bacteria and/or *Bacillus*. In one embodiment the method results in an increase in the level of lactic acid bacteria and/or *Bacillus* the hatcher. In one embodiment the method results in an increase in the level of lactic acid bacteria and/or *Bacillus* in the GIT of the chick. In one embodiment the method results in an increase in the level of lactic acid bacteria and/or *Bacillus* in the hatcher and in the GIT of the chick.

In another embodiment of the method the administration results in that the bacterial bloom in the poultry hatcher cabinet is modified or controlled. This can mean that the level of pathogenic bacteria is decreased. Pathogenic bacteria in this connection can in one embodiment be selected from the group consisting of coliform bacteria, *Salmonella, E. coli, Pseudomonas, Streptococcus, Staphylococcus,* and *Enterococcus*. Preferably the method results in a shift of the environmental microbiota of the poultry to one of more beneficial probiotic bacteria. In one embodiment of the method the administration results in a decrease in pathogenic bacteria which are selected from the group consisting of coliform bacteria, *Salmonella, E. coli, Pseudomonas, Streptococcus, Staphylococcus,* and *Enterococcus*. In one embodiment of the method the administration results in a decrease in pathogenic bacteria which are selected from the group consisting of coliform bacteria, *Salmonella* and *E. coli*.

In a further embodiment of the method the administration results in that the level of coliform bacteria in the hatchery is lowered. In a further embodiment of the method the administration results in that the level of coliform bacteria in the hatcher cabinet is lowered. In a yet further embodiment of the method the administration results in that the level of coliform bacteria in the hatchery is lowered at least 25%, such as at least 30% or at least 40%. In a yet further embodiment of the method the administration results in that the level of coliform bacteria in the hatcher cabinet is lowered at least 25% such as at least 30% or at least 40%. In a yet further embodiment of the method the administration results in that the level of coliform bacteria in the hatchery is lowered at least 50%. In a yet further embodiment of the method the administration results in that the level of coliform bacteria in the hatcher cabinet is lowered at least 50%. In a further embodiment of the method the administration results in that the level of coliform bacteria in the hatchery is lowered at least 1 log. In a further embodiment of the method the administration results in that the level of coliform bacteria in the hatcher cabinet is lowered at least 1 log. In a further embodiment of the method the administration results in that the level of coliform bacteria in the hatchery is lowered at least 2 logs. In a further embodiment of the method the administration results in that the level of coliform bacteria in the hatcher cabinet is lowered at least 2 logs.

In a preferred embodiment the method relates to treatment of chickens and/or turkeys. In one embodiment the method relates to treatment of broilers and/or layers.

In a preferred embodiment the method relates to administering one or more probiotic(s) in the poultry hatcher cabinet before hatching. Alternatively, the method relates to administering one or more probiotic(s) in the poultry hatcher cabinet after hatching such as within 24 hours after hatching such as within 20, 18, 16, 14, 12, 10, 8, 6, 4, 2, 1 hours after hatching. In one embodiment some eggs are hatched and some are not hatched. Preferably less than 90% are hatched such as less than 80%, 70%, 60%, 50%, 40%, 30%, 20%, 10%, 5% or less than 1% are hatched when the one or more probiotic(s) are administered in the poultry hatcher cabinet.

The administration can be repeated one or more times, e.g., before and/or after the hatching such as 2, 3, 4, 5, 6, 7, 8, 9, or 10 repeats. Alternatively, the administration can be continuously through the time in the hatcher cabinet.

In a preferred embodiment of the method the one or more probiotic(s) have one or more properties selected from the group consisting of
i) robustly form spores of high quality in commercial scale solid-state fermentation,
ii) robustly grow in submerged fermentation and maintain stability after lyophilization,
iii) successfully germinate in and colonize the poultry gastrointestinal tract,
iv) improve poultry performance parameters (such as mortality, Body Weight Gain (BWG) and/or Feed Conversion Ratio (FCR))
v) improve poultry performance parameters of the young chicks (such as, e.g., improvement of body weight and/or uniformity of the chicks as measured at days 7 to 10),
vi) inhibit common poultry pathogens both in vitro and in vivo studies and
vii) maintain viability in the hatcher cabinet environment.

In another preferred embodiment of the method the one or more probiotic(s) are able to reduce the incidence of Gram negative bacteria in the hatcher cabinet environment and/or decrease end-of-life mortality, and/or improve feed conversion, and/or increase body weight gain in poultry.

The application of probiotic bacteria in the hatcher cabinets preferably provides pioneer colonizers to the gut before the chick can be exposed to non-beneficial or pathogenic bacteria, which may have lifelong deleterious effects.

The application method preferably provides uniform treatment to all chicks in the hatcher cabinet, likely improving flock uniformity.

Application by dry spray eliminates storage (shelf life) and application concerns which may accompany a wet spray application. The isolates and preparation used have been shown to be stable in the hatcher cabinet environment for the time period needed.

Compositions

In a preferred aspect the invention relates to a composition comprising one or more *Bacillus* strains and one or more lactic acid bacteria strains.

In a preferred embodiment with respect to the composition the one or more lactic acid bacteria is selected from the group consisting of
i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.

In a preferred embodiment with respect to the composition the one or more *Bacillus* is selected from the group consisting of
i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof, ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.

In a specific embodiment with respect to the composition the one or more lactic acid bacteria is selected from the group consisting of i) *Pediococcus acidilactici* FM18 deposited as NRRL Deposit Number B-50964, ii) *Pediococcus acidilactici* TY036 deposited as NRRL Deposit Number B-50959, and iii) *Enterococcus faecium* MFF109 deposited as NRRL Deposit Number B-50960.

In another specific embodiment with respect to the composition the one or more *Bacillus* is selected from the group consisting of i) *Bacillus amyloliquefaciens* AM0904 deposited as NRRL Deposit Number B-50914, ii) *Bacillus amyloliquefaciens* NP122 deposited as NRRL Deposit Number B-50910, and iii) *Bacillus amyloliquefaciens* B2 deposited as NRRL Deposit Number B-50908.

In a specific embodiment with respect to the composition comprises one or more lactic acid bacteria selected from the group consisting of i) *Pediococcus acidilactici* FM18 deposited as NRRL Deposit Number B-50964, ii) *Pediococcus acidilactici* TY036 deposited as NRRL Deposit Number B-50959, and iii) *Enterococcus faecium* MFF109 deposited as NRRL Deposit Number B-50960;

and one or more *Bacillus* selected from the group consisting of i) *Bacillus amyloliquefaciens* AM0904 deposited as NRRL Deposit Number B-50914, ii) *Bacillus amyloliquefaciens* NP122 deposited as NRRL Deposit Number B-50910, and iii) *Bacillus amyloliquefaciens* B2 deposited as NRRL Deposit Number B-50908.

In a preferred embodiment with respect to the composition the one or more *Bacillus* strains and one or more lactic acid bacteria strains comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

In a preferred embodiment the *Bacillus* strains and/or the lactic acid bacteria strains according to the invention or the composition according to the invention has one or more properties selected from the group consisting of i) robustly form spores of high quality in commercial scale solid-state fermentation, ii) robustly grow in submerged fermentation and maintain stability after lyophilization, iii) successfully germinate in and colonize the poultry gastrointestinal tract, iv) improve poultry performance parameters (such as mortality, BWG, FCR)

v) inhibit common poultry pathogens both in vitro and in vivo studies and vi) maintain viability in the hatcher cabinet environment.

In another preferred embodiment the *Bacillus* strains and/or the lactic acid bacteria strains according to the invention or the composition according to the invention is able to reduce the incidence of Gram negative bacteria in the hatcher cabinet environment and/or decrease end-of-life mortality, and/or improve feed conversion, and/or increase body weight gain in poultry.

In a specific embodiment the composition comprises a carrier such as a carrier comprising or consisting of: a) wheat bran flakes and/or b) calcium carbonate and/or c) an anti-caking/flow agent.

The *Bacillus* isolates (B2, NP122, AM0904) were isolated from poultry and environmental samples and evaluated for their ability to grow and sporulate robustly in a solid-state fermentation system. They were also evaluated for their ability to germinate within the chicken gastrointestinal tract, form biofilms, and inhibit common poultry and food-related pathogens by both in vitro and in vivo experimentation.

The *Pedicoccus* isolates (PVG-18, TY036) were isolated from poultry samples and evaluated for their ability to grow in a submerged fermentation system and maintain stability after lyophilization. They were also evaluated for their ability to inhibit common poultry pathogens by both in vitro and in vivo experimentation. These were selected for suppression of pathogens in neonatal poultry and for early stimulation of the GIT respectively.

Preferably the probiotic is isolated.

Preferred Embodiments

Preferred embodiments of the invention are given in the set of items herein below.

1. A method for improving one or more performance parameter(s) of poultry comprising the step of administering one or more probiotic(s) in the poultry hatcher cabinet.

2. The method of item 1, wherein the administering is performed by spraying the one or more probiotic(s) into the poultry hatcher cabinet.

3. The method of item 1 or 2, wherein the one or more probiotic(s) is a powder formulation such as a dry powder formulation.

4. The method of any of items 1-3, wherein the one or more probiotic(s) comprises one or more *Bacillus* strains.

5. The method of any of items 1-4, wherein the one or more probiotic(s) comprises one or more lactic acid bacteria strains.

6. The method of any of items 1-5, wherein the one or more probiotic(s) comprises one or more *Bacillus* strains and one or more lactic acid bacteria strains.

7. The method of any of items 1-6, wherein the one or more probiotic(s) comprises one or more lactic acid bacteria selected from the group consisting of
    i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
    ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
    iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.

8. The method of any of items 1-7, wherein the one or more probiotic(s) comprises one or more *Bacillus* selected from the group consisting of
    i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof,
    ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and
    iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.

9. The method of any of items 1-8, wherein the one or more probiotic(s) comprises one or more lactic acid bacteria selected from the group consisting of
    i) *Pediococcus acidilactici* FM18 deposited as NRRL Deposit Number B-50964,
    ii) *Pediococcus acidilactici* TY036 deposited as NRRL Deposit Number B-50959, and
    iii) *Enterococcus faecium* MFF109 deposited as NRRL Deposit Number B-50960.

10. The method of any items 1-9, wherein the one or more probiotic(s) comprises one or more *Bacillus* selected from the group consisting of
    i) *Bacillus amyloliquefaciens* AM0904 deposited as NRRL Deposit Number B-50914,
    ii) *Bacillus amyloliquefaciens* NP122 deposited as NRRL Deposit Number B-50910, and
    iii) *Bacillus amyloliquefaciens* B2 deposited as NRRL Deposit Number B-50908.

11. The method of any of items 1-10, wherein the one or more probiotic(s) comprises a 16S rDNA sequence selected from the group consisting of:
    (a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
    (b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
    (c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;
    (d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;
    (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and
    (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

12. The method of any of items 1-11, wherein the one or more performance parameter(s) is selected from the group consisting of body weight gain, growth rate, feed conversion rate and overall health.

13. The method of any of items 1-12, wherein the bacterial bloom in the poultry hatcher cabinet is modified or controlled.

14. The method of any of items 1-13, wherein the poultry is chickens and/or turkeys.

15. The method of any of items 1-14, wherein the one or more *Bacillus* strains and one or more lactic acid bacteria strains are administered simultaneously.

16. The method of any of items 1-15, wherein the one or more *Bacillus* strains and one or more lactic acid bacteria strains are administered subsequently in any order.

17. The method of any of items 1-16, wherein the one or more *Bacillus* strains and one or more lactic acid bacteria strains are administered subsequently and wherein the one or more *Bacillus* strains is administered before the one or more lactic acid bacteria strains.

18. The method of any of items 1-17, wherein the one or more *Bacillus* strains and one or more lactic acid bacteria strains are administered subsequently and wherein the one or more lactic acid bacteria strains is administered before the one or more *Bacillus* strains.

19. The method of any of items 1-18, wherein the one or more *Bacillus* strains is administered as a dry formulation.

20. The method of any of items 1-19, wherein the one or more *Bacillus* strains is administered as a wet formulation such as an aqueous formulation.

21. The method of any of items 1-20, wherein the one or more lactic acid bacteria strains is administered as a dry formulation.

22. The method of any of items 1-21, wherein the one or more lactic acid bacteria strains is administered as a wet formulation such as an aqueous formulation.
23. The method of any of items 1-22, wherein the one or more *Bacillus* strains is administered more than once such as 2, 3, 4, 5, 6, 7 8, 9, 10 or more than 10 times.
24. The method of any of items 1-23, wherein the one or more lactic acid bacteria strains is administered more than once such as 2, 3, 4, 5, 6, 7 8, 9, 10 or more than 10 times.
25. The method of any of items 1-24, wherein the one or more *Bacillus* strains is administered in a dose selected from the group consisting of $1\times10^5$ to $1\times10^6$ CFU *Bacillus* per bird, $1\times10^6$ to $1\times10^7$ CFU *Bacillus* per bird, $1\times10^7$ to $1\times10^8$ CFU *Bacillus* per bird, $1\times10^8$ to $1\times10^9$ CFU *Bacillus* per bird, $1\times10^9$ to $1\times10^{10}$ CFU *Bacillus* per bird, $1\times10^{10}$ to $1\times10^{11}$ CFU *Bacillus* per bird, $1\times10^{11}$ to $1\times10^{12}$ CFU *Bacillus* per bird, or any combination thereof.
26. The method of any of items 1-25, wherein the one or more lactic acid bacteria strains is administered in a dose selected from the group consisting of $1\times10^4$ to $1\times10^5$ CFU lactic acid bacteria per bird, $1\times10^5$ to $1\times10^6$ CFU lactic acid bacteria per bird, $1\times10^6$ to $1\times10^7$ CFU lactic acid bacteria per bird, $1\times10^7$ to $1\times10^8$ CFU lactic acid bacteria per bird, $1\times10^9$ to $1\times10^{10}$ CFU lactic acid bacteria per bird, $1\times10^{10}$ to $1\times10^{11}$ CFU lactic acid bacteria per bird, $1\times10^{11}$ to $1\times10^{12}$ CFU lactic acid bacteria per bird, or any combination thereof.
27. The method of any of items 1-26, wherein the one or more *Bacillus* and/or the one or more lactic acid bacteria strains is administered at the time of transfer to the hatcher cabinet.
28. The method of any of items 1-27, wherein the one or more *Bacillus* and/or the one or more lactic acid bacteria strains is administered at a time selected from the group consisting of from 10% pip to 20% pip, from 20% pip to 30% pip, from 30% pip to 40% pip, from 40% pip to 50% pip, from 50% pip to 60% pip, from 60% pip to 70% pip, from 70% pip to 80% pip, from 80% pip to 90% pip, from 90% pip to 100% pip, or any combination thereof.
29. The method of any of items 1-28, wherein the one or more *Bacillus* and/or the one or more lactic acid bacteria strains is administered at a time selected from the group consisting of from 10% hatch to 20% hatch, from 20% hatch to 30% hatch, from 30% hatch to 40% hatch, from 40% hatch to 50% hatch, from 50% hatch to 60% hatch, from 60% hatch to 70% hatch, from 70% hatch to 80% hatch, from 80% hatch to 90% hatch, from 90% hatch to 100% hatch, or any combination thereof.
30. A composition comprising one or more *Bacillus* strains and one or more lactic acid bacteria strains.
31. The composition of item 30, wherein the one or more lactic acid bacteria is selected from the group consisting of
  i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
  ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
  iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.
32. The composition of item 30 or 31, wherein the one or more *Bacillus* is selected from the group consisting of
  i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof,
  ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and
  iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.
33. The composition of any of items 30-32, wherein the one or more lactic acid bacteria is selected from the group consisting of
  i) *Pediococcus acidilactici* FM18 deposited as NRRL Deposit Number B-50964,
  ii) *Pediococcus acidilactici* TY036 deposited as NRRL Deposit Number B-50959, and
  iii) *Enterococcus faecium* MFF109 deposited as NRRL Deposit Number B-50960.
34. The composition of any of items 30-33, wherein the one or more *Bacillus* is selected from the group consisting of
  i) *Bacillus amyloliquefaciens* AM0904 deposited as NRRL Deposit Number B-50914,
  ii) *Bacillus amyloliquefaciens* NP122 deposited as NRRL Deposit Number B-50910, and
  iii) *Bacillus amyloliquefaciens* B2 deposited as NRRL Deposit Number B-50908.
35. The composition of any of items 30-34, wherein the one or more *Bacillus* strains and one or more lactic acid bacteria strains comprise a 16S rDNA sequence selected from the group consisting of:
  (a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
  (b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
  (c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;
  (d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;
  (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.
36. The composition of any of items 30-35, wherein the one or more lactic acid bacteria are on spore form.
37. The composition of any of items 30-36, wherein the one or more *Bacillus* are on spore form.
38. The composition of any of items 30-37, wherein the one or more lactic acid bacteria are isolated.
39. The composition of any of items 30-38, wherein the one or more *Bacillus* are isolated.
40. The composition of any of items 30-39, wherein the composition is a dry formulation.
41. The composition of any of items 30-39, wherein the composition is a wet formulation.

Further Preferred Embodiments

Further preferred embodiments of the invention are given in the set of items herein below.
1. A method for improving one or more performance parameter(s) of poultry comprising the step of administering one or more probiotic(s) in the poultry hatcher cabinet.
2. The method of item 1, wherein the administering is performed by spraying the one or more probiotic(s) into the poultry hatcher cabinet.
3. The method of item 1 or 2, wherein the one or more probiotic(s) is a powder formulation such as a dry powder formulation.
4. The method of any of items 1-3, wherein the one or more probiotic(s) comprises one or more *Bacillus* strains.
5. The method of any of items 1-4, wherein the one or more probiotic(s) comprises one or more lactic acid bacteria strains.
6. The method of any of items 1-5, wherein the one or more probiotic(s) comprises one or more *Bacillus* strains and one or more lactic acid bacteria strains.
7. The method of any of items 1-6, wherein the one or more probiotic(s) comprises one or more lactic acid bacteria selected from the group consisting of
   i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
   ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
   iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.
8. The method of any of items 1-7, wherein the one or more probiotic(s) comprises one or more lactic acid bacteria selected from the group consisting of
   i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, and
   ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof.
9. The method of any of items 1-8, wherein the one or more probiotic(s) comprises one or more *Bacillus* selected from the group consisting of
   i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof,
   ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and
   iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.
10. The method of any of items 1-7 or 9, wherein the one or more probiotic(s) comprises one or more lactic acid bacteria selected from the group consisting of
    i) *Pediococcus acidilactici* FM18 deposited as NRRL Deposit Number B-50964,
    ii) *Pediococcus acidilactici* TY036 deposited as NRRL Deposit Number B-50959, and
    iii) *Enterococcus faecium* MFF109 deposited as NRRL Deposit Number B-50960.
11. The method of any of items 1-10, wherein the one or more probiotic(s) comprises one or more lactic acid bacteria selected from the group consisting of
    i) *Pediococcus acidilactici* FM18 deposited as NRRL Deposit Number B-50964, and
    ii) *Pediococcus acidilactici* TY036 deposited as NRRL Deposit Number B-50959, and
12. The method of any of items 1-11, wherein the one or more probiotic(s) comprises one or more *Bacillus* selected from the group consisting of
    i) *Bacillus amyloliquefaciens* AM0904 deposited as NRRL Deposit Number B-50914,
    ii) *Bacillus amyloliquefaciens* NP122 deposited as NRRL Deposit Number B-50910, and
    iii) *Bacillus amyloliquefaciens* B2 deposited as NRRL Deposit Number B-50908.
13. The method of any of items 1-7, 9-10 or 12, wherein the one or more probiotic(s) comprises a 16S rDNA sequence selected from the group consisting of:
    (a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
    (b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
    (c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;
    (d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

14. The method of any of items 1-13, wherein the one or more probiotic(s) comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

15. The method of any of items 1-14, wherein the one or more performance parameter(s) is selected from the group consisting of body weight gain, growth rate, feed conversion rate and overall health.

16. The method of any of items 1-15, wherein the bacterial bloom in the poultry hatcher cabinet is modified or controlled.

17. The method of any of items 1-16 to the extent possible, wherein the bacterial bloom in the poultry hatcher cabinet is modified, controlled or lowered compared to the bacterial bloom in a poultry hatcher cabinet where the method has not been applied.

18. The method of any of items 1-17, wherein the poultry is chickens and/or turkeys.

19. The method of any of items 1-18, wherein the one or more *Bacillus* strains and one or more lactic acid bacteria strains are administered simultaneously.

20. The method of any of items 1-18, wherein the one or more *Bacillus* strains and one or more lactic acid bacteria strains are administered subsequently in any order.

21. The method of any of items 1-18, wherein the one or more *Bacillus* strains and one or more lactic acid bacteria strains are administered subsequently and wherein the one or more *Bacillus* strains is administered before the one or more lactic acid bacteria strains.

22. The method of any of items 1-18, wherein the one or more *Bacillus* strains and one or more lactic acid bacteria strains are administered subsequently and wherein the one or more lactic acid bacteria strains is administered before the one or more *Bacillus* strains.

23. The method of any of items 1-18, wherein the one or more *Bacillus* strains and one or more lactic acid bacteria strains are administered in successive steps and wherein the one or more *Bacillus* strains is administered before the one or more lactic acid bacteria strains.

24. The method of any of items 1-18, wherein the one or more *Bacillus* strains and one or more lactic acid bacteria strains are administered in successive steps and wherein the one or more lactic acid bacteria strains is administered before the one or more *Bacillus* strains.

25. The method of any of items 1-24, wherein the one or more *Bacillus* strains is administered as a dry formulation.

26. The method of any of items 1-24, wherein the one or more *Bacillus* strains is administered as a wet formulation such as an aqueous formulation.

27. The method of any of items 1-26, wherein the one or more lactic acid bacteria strains is administered as a dry formulation.

28. The method of any of items 1-26, wherein the one or more lactic acid bacteria strains is administered as a wet formulation such as an aqueous formulation.

29. The method of any of items 1-28, wherein the one or more *Bacillus* strains is administered more than once such as 2, 3, 4, 5, 6, 7 8, 9, 10 or more than 10 times.

30. The method of any of items 1-28, wherein the one or more lactic acid bacteria strains is administered more than once such as 2, 3, 4, 5, 6, 7 8, 9, 10 or more than 10 times.

31. The method of any of items 1-30, wherein the one or more *Bacillus* strains is administered in a dose selected from the group consisting of $1\times10^5$ to $1\times10^6$ CFU *Bacillus* per bird, $1\times10^6$ to $1\times10^7$ CFU *Bacillus* per bird, $1\times10^7$ to $1\times10^8$ CFU *Bacillus* per bird, $1\times10^8$ to $1\times10^9$ CFU *Bacillus* per bird, $1\times10^9$ to $1\times10^{10}$ CFU *Bacillus* per bird, $1\times10^{10}$ to $1\times10^{11}$ CFU *Bacillus* per bird, $1\times10^{11}$ to $1\times10^{12}$ CFU *Bacillus* per bird, or any combination thereof.

32. The method of any of items 1-31, wherein the one or more lactic acid bacteria strains is administered in a dose selected from the group consisting of $1\times10^4$ to $1\times10^5$ CFU lactic acid bacteria per bird, $1\times10^5$ to $1\times10^6$ CFU lactic acid bacteria per bird, $1\times10^6$ to $1\times10^7$ CFU lactic acid bacteria per bird, $1\times10^7$ to $1\times10^8$ CFU lactic acid bacteria per bird, $1\times10^9$ to $1\times10^{10}$ CFU lactic acid bacteria per bird, $1\times10^{10}$ to $1\times10^{11}$ CFU lactic acid bacteria per bird, $1\times10^{11}$ to $1\times10^{12}$ CFU lactic acid bacteria per bird, or any combination thereof.

33. The method of any of items 1-32, wherein the one or more *Bacillus* and/or the one or more lactic acid bacteria strains is administered at the time of transfer to the hatcher cabinet.

34. The method of any of items 1-33, wherein the one or more *Bacillus* and/or the one or more lactic acid bacteria strains is administered at a time selected from the group consisting of from 10% pip to 20% pip, from 20% pip to 30% pip, from 30% pip to 40% pip, from 40% pip to 50% pip, from 50% pip to 60% pip, from 60% pip to 70% pip, from 70% pip to 80% pip, from 80% pip to 90% pip, from 90% pip to 100% pip, or any combination thereof.

35. The method of any of items 1-34, wherein the one or more *Bacillus* and/or the one or more lactic acid bacteria strains is administered at a time selected from the group consisting of from 10% hatch to 20% hatch, from 20% hatch to 30% hatch, from 30% hatch to 40% hatch, from 40% hatch to 50% hatch, from 50% hatch to 60% hatch, from 60% hatch to 70% hatch, from 70% hatch to 80% hatch, from 80% hatch to 90% hatch, from 90% hatch to 100% hatch, or any combination thereof.

36. A composition comprising one or more *Bacillus* strains and/or one or more lactic acid bacteria strains.

37. A composition of item 36 which comprises one or more *Bacillus* strains and one or more lactic acid bacteria strains.

38. A composition of item 36 or 37 which further comprises a silicate flow aid.

39. The composition of any of items 36-38, wherein the one or more lactic acid bacteria is selected from the group consisting of
   i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
   ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
   iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.

40. The composition of any of items 36-39, wherein the one or more lactic acid bacteria is selected from the group consisting of
   i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, and
   ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof.

41. The composition of any of items 36-40, wherein the one or more *Bacillus* is selected from the group consisting of
   i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof,
   ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and
   iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.

42. The composition of any of items 36-39 or 41, wherein the one or more lactic acid bacteria is selected from the group consisting of
   i) *Pediococcus acidilactici* FM18 deposited as NRRL Deposit Number B-50964,
   ii) *Pediococcus acidilactici* TY036 deposited as NRRL Deposit Number B-50959, and
   iii) *Enterococcus faecium* MFF109 deposited as NRRL Deposit Number B-50960.

43. The composition of any of items 36-42, wherein the one or more lactic acid bacteria is selected from the group consisting of
   i) *Pediococcus acidilactici* FM18 deposited as NRRL Deposit Number B-50964, and
   ii) *Pediococcus acidilactici* TY036 deposited as NRRL Deposit Number B-50959.

44. The composition of any of items 36-43, wherein the one or more *Bacillus* is selected from the group consisting of
   i) *Bacillus amyloliquefaciens* AM0904 deposited as NRRL Deposit Number B-50914,
   ii) *Bacillus amyloliquefaciens* NP122 deposited as NRRL Deposit Number B-50910, and
   iii) *Bacillus amyloliquefaciens* B2 deposited as NRRL Deposit Number B-50908.

45. The composition of any of items 36-39, 41, 42 or 44, wherein the one or more *Bacillus* strains and one or more lactic acid bacteria strains comprise a 16S rDNA sequence selected from the group consisting of:
   (a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
   (b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
   (c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;
   (d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;
   (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and
   (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

46. The composition of any of items 36-45, wherein the one or more *Bacillus* strains and one or more lactic acid bacteria strains comprise a 16S rDNA sequence selected from the group consisting of:
   (a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
   (b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
   (c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

47. The composition of any of items 36-46, wherein the one or more lactic acid bacteria are on spore form.
48. The composition of any of items 36-47, wherein the one or more *Bacillus* are on spore form.
49. The composition of any of items 36-48, wherein the one or more lactic acid bacteria are isolated.
50. The composition of any of items 36-49, wherein the one or more *Bacillus* are isolated.
51. The composition of any of items 36-50, wherein the composition is a dry formulation.
52. The composition of any of items 36-51, wherein the composition is a wet formulation.
53. A probiotic improving one or more performance parameter(s) of poultry.
54. The probiotic of item 53, wherein the probiotic comprises one or more *Bacillus* strains.
55. The probiotic of item 53 or 54, wherein the probiotic comprises one or more lactic acid bacteria strains.
56. The probiotic of any of items 53-55, wherein the probiotic comprises one or more *Bacillus* strains or one or more lactic acid bacteria strains.
57. The probiotic of any of items 53-56, which comprises a further bacteria strain.
58. The probiotic of any of items 53-57, wherein the probiotic comprises one or more *Bacillus* strains and one or more lactic acid bacteria strains.
59. The probiotic of any of items 53-58, wherein the probiotic comprises one or more lactic acid bacteria selected from the group consisting of
    i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
    ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
    iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.
60. The probiotic of any of items 53-59, wherein the probiotic comprises one or more lactic acid bacteria selected from the group consisting of
    i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, and
    ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof.
61. The probiotic of any of items 53-60, wherein the probiotic comprises one or more *Bacillus* selected from the group consisting of
    i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof,
    ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and
    iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.
62. The probiotic of any of items 53-59 or 61, wherein the probiotic comprises one or more lactic acid bacteria selected from the group consisting of
    i) *Pediococcus acidilactici* FM18 deposited as NRRL Deposit Number B-50964,
    ii) *Pediococcus acidilactici* TY036 deposited as NRRL Deposit Number B-50959, and
    iii) *Enterococcus faecium* MFF109 deposited as NRRL Deposit Number B-50960.
63. The probiotic of any of items 53-62, wherein the probiotic comprises one or more lactic acid bacteria selected from the group consisting of
    i) *Pediococcus acidilactici* FM18 deposited as NRRL Deposit Number B-50964, and
    ii) *Pediococcus acidilactici* TY036 deposited as NRRL Deposit Number B-50959, and
64. The probiotic of any of items 53-63, wherein the probiotic comprises one or more *Bacillus* selected from the group consisting of
    i) *Bacillus amyloliquefaciens* AM0904 deposited as NRRL Deposit Number B-50914,
    ii) *Bacillus amyloliquefaciens* NP122 deposited as NRRL Deposit Number B-50910, and
    iii) *Bacillus amyloliquefaciens* B2 deposited as NRRL Deposit Number B-50908.
65. The probiotic of any of items 53-59, 61, 62 or 64, wherein the probiotic comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

66. The probiotic of any of items 53-65, wherein the probiotic comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

67. A probiotic for use in the treatment of poultry for improving one or more performance parameter(s), wherein the probiotic is administered in the poultry hatcher cabinet.

68. The probiotic of item 67, wherein the administration is performed by spraying the one or more probiotic(s) into the poultry hatcher cabinet.

69. The probiotic of item 67 or 68, wherein the probiotic is a powder formulation such as a dry powder formulation.

70. The probiotic of any of items 67-69, wherein the probiotic comprises one or more *Bacillus* strains.

71. The probiotic of any of items 67-70, wherein the probiotic comprises one or more lactic acid bacteria strains.

72. The probiotic of any of items 67-71, wherein the probiotic comprises one or more *Bacillus* strains and one or more lactic acid bacteria strains.

73. The probiotic of any of items 67-72, wherein the probiotic comprises one or more lactic acid bacteria selected from the group consisting of i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.

74. The probiotic of any of items 67-73, wherein the probiotic comprises one or more lactic acid bacteria selected from the group consisting of i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, and ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof.

75. The probiotic of any of items 67-74, wherein the probiotic comprises one or more *Bacillus* selected from the group consisting of i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof, ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.

76. The probiotic of any of items 67-73 or 75, wherein the probiotic comprises one or more lactic acid bacteria selected from the group consisting of i) *Pediococcus acidilactici* FM18 deposited as NRRL Deposit Number B-50964, ii) *Pediococcus acidilactici* TY036 deposited as NRRL Deposit Number B-50959, and iii) *Enterococcus faecium* MFF109 deposited as NRRL Deposit Number B-50960.

77. The probiotic of any of items 67-76, wherein the probiotic comprises one or more lactic acid bacteria selected from the group consisting of i) *Pediococcus acidilactici* FM18 deposited as NRRL Deposit Number B-50964, and ii) *Pediococcus acidilactici* TY036 deposited as NRRL Deposit Number B-50959, and 78. The probiotic of any of items 67-77, wherein the probiotic comprises one or more *Bacillus* selected from the group consisting of i) *Bacillus amyloliquefaciens* AM0904 deposited as NRRL Deposit Number B-50914, ii) *Bacillus amyloliquefaciens* NP122 deposited as NRRL Deposit Number B-50910, and iii) *Bacillus amyloliquefaciens* B2 deposited as NRRL Deposit Number B-50908.

79. The probiotic of any of items 67-73, 75, 76 or 78, wherein the probiotic comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

80. The probiotic of any of items 67-79, wherein the probiotic comprises a 16S rDNA sequence selected from the group consisting of:

(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;

(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;

(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;

(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and (e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

81. The probiotic of any of items 67-80, wherein the one or more performance parameter(s) is selected from the group consisting of body weight gain, growth rate, feed conversion rate and overall health.

82. The probiotic of any of items 67-81, wherein the bacterial bloom in the poultry hatcher cabinet is modified or controlled.

83. The probiotic of any of items 67-82, wherein the bacterial bloom in the poultry hatcher cabinet is modified, controlled or lowered compared to the bacterial bloom in a poultry hatcher cabinet where the probiotic has not been applied.

84. The probiotic of any of items 67-83, wherein the poultry is chickens and/or turkeys.

85. The probiotic of any of items 67-84, wherein the one or more *Bacillus* strains and one or more lactic acid bacteria strains are administered simultaneously.

86. The probiotic of any of items 67-84, wherein the one or more *Bacillus* strains and one or more lactic acid bacteria strains are administered subsequently in any order.

87. The probiotic of any of items 67-84, wherein the one or more *Bacillus* strains and one or more lactic acid bacteria strains are administered subsequently and wherein the one or more *Bacillus* strains is administered before the one or more lactic acid bacteria strains.

88. The probiotic of any of items 67-84, wherein the one or more *Bacillus* strains and one or more lactic acid bacteria strains are administered subsequently and wherein the one or more lactic acid bacteria strains is administered before the one or more *Bacillus* strains.

89. The probiotic of any of items 67-84, wherein the one or more *Bacillus* strains and one or more lactic acid bacteria strains are administered in successive steps and wherein the one or more *Bacillus* strains is administered before the one or more lactic acid bacteria strains.

90. The probiotic of any of items 67-84, wherein the one or more *Bacillus* strains and one or more lactic acid bacteria strains are administered in successive steps and wherein the one or more lactic acid bacteria strains is administered before the one or more *Bacillus* strains.

91. The probiotic of any of items 67-90, wherein the one or more *Bacillus* strains is administered as a dry formulation.

92. The probiotic of any of items 67-91, wherein the one or more *Bacillus* strains is administered as a wet formulation such as an aqueous formulation.

93. The probiotic of any of items 67-92, wherein the one or more lactic acid bacteria strains is administered as a dry formulation.

94. The probiotic of any of items 67-93, wherein the one or more lactic acid bacteria strains is administered as a wet formulation such as an aqueous formulation.

95. The probiotic of any of items 67-94, wherein the one or more *Bacillus* strains is administered more than once such as 2, 3, 4, 5, 6, 7 8, 9, 10 or more than 10 times.

96. The probiotic of any of items 67-94, wherein the one or more lactic acid bacteria strains is administered more than once such as 2, 3, 4, 5, 6, 7 8, 9, 10 or more than 10 times.

97. The probiotic of any of items 67-96, wherein the one or more *Bacillus* strains is administered in a dose selected from the group consisting of $1\times10^5$ to $1\times10^6$ CFU *Bacillus* per bird, $1\times10^6$ to $1\times10^7$ CFU *Bacillus* per bird, $1\times10^7$ to $1\times10^8$ CFU *Bacillus* per bird, $1\times10^8$ to $1\times10^9$ CFU *Bacillus* per bird, $1\times10^9$ to $1\times10^{10}$ CFU *Bacillus* per bird, $1\times10^{10}$ to $1\times10^{11}$ CFU *Bacillus* per bird, $1\times10^{11}$ to $1\times10^{12}$ CFU *Bacillus* per bird, or any combination thereof.

98. The probiotic of any of items 67-97, wherein the one or more lactic acid bacteria strains is administered in a dose selected from the group consisting of $1\times10^4$ to $1\times10^5$ CFU lactic acid bacteria per bird, $1\times10^5$ to $1\times10^6$ CFU lactic acid bacteria per bird, $1\times10^6$ to $1\times10^7$ CFU lactic acid bacteria per bird, $1\times10^7$ to $1\times10^8$ CFU lactic acid bacteria per bird, $1\times10^8$ to $1\times10^9$ CFU lactic acid bacteria per bird, $1\times10^9$ to $1\times10^{10}$ CFU lactic acid bacteria per bird, $1\times10^{10}$ to $1\times10^{11}$ CFU lactic acid bacteria per bird, $1\times10^{11}$ to $1\times10^{12}$ CFU lactic acid bacteria per bird, or any combination thereof.

99. The probiotic of any of items 67-98, wherein the one or more *Bacillus* and/or the one or more lactic acid bacteria strains is administered at the time of transfer to the hatcher cabinet.

100. The probiotic of any of items 67-99, wherein the one or more *Bacillus* and/or the one or more lactic acid bacteria strains is administered at a time selected from the group consisting of from 10% pip to 20% pip, from 20% pip to 30% pip, from 30% pip to 40% pip, from 40% pip to 50% pip, from 50% pip to 60% pip, from 60% pip to 70% pip, from 70% pip to 80% pip, from 80% pip to 90% pip, from 90% pip to 100% pip, or any combination thereof.

101. The probiotic of any of items 67-100, wherein the one or more *Bacillus* and/or the one or more lactic acid bacteria strains is administered at a time selected from the group consisting of from 10% hatch to 20% hatch, from 20% hatch to 30% hatch, from 30% hatch to 40% hatch, from 40% hatch to 50% hatch, from 50% hatch to 60% hatch, from 60% hatch to 70% hatch, from 70% hatch to 80% hatch, from 80% hatch to 90% hatch, from 90% hatch to 100% hatch, or any combination thereof.

102. Use of one or more probiotic(s) in the manufacture of a medicament for improving one or more performance parameter(s) of poultry wherein the one or more probiotic(s) is administered to the poultry in the poultry hatcher cabinet.

103. Use of one or more probiotic(s) for improving one or more performance parameter(s) of poultry comprising the step of administering the one or more probiotic(s) to the poultry in the poultry hatcher cabinet.

104. The use of item 102 or 103, wherein the administering is performed by spraying the one or more probiotic(s) into the poultry hatcher cabinet.

105. The use of any of items 102-104, wherein the one or more probiotic(s) is a powder formulation such as a dry powder formulation.

106. The use of any of items 102-105, wherein the one or more probiotic(s) comprises one or more *Bacillus* strains.

107. The use of any of items 102-106, wherein the one or more probiotic(s) comprises one or more lactic acid bacteria strains.

108. The use of any of items 102-107, wherein the one or more probiotic(s) comprises one or more *Bacillus* strains and one or more lactic acid bacteria strains.

109. The use of any of items 102-108, wherein the one or more probiotic(s) comprises one or more lactic acid bacteria selected from the group consisting of
   i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof,
   ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof, and
   iii) *Enterococcus faecium* MFF109 deposited as NRRL Deposit Number B-50960, a strain having all of the identifying characteristics of *Enterococcus faecium* MFF109 deposited as NRRL Deposit Number B-50960 or a mutant thereof.

110. The use of any of items 102-109, wherein the one or more probiotic(s) comprises one or more lactic acid bacteria selected from the group consisting of
   i) *Pediococcus acidilactici* FM18 deposited as NRRL Deposit Number B-50964, a strain having all of the identifying characteristics of *Pediococcus acidilactici* FM18 deposited as NRRL Deposit Number B-50964 or a mutant thereof, and
   ii) *Pediococcus acidilactici* TY036 deposited as NRRL Deposit Number B-50959, a strain having all of the identifying characteristics of *Pediococcus acidilactici* TY036 deposited as NRRL Deposit Number B-50959 or a mutant thereof.

111. The use of any of items 102-110, wherein the one or more probiotic(s) comprises one or more *Bacillus* selected from the group consisting of
   i) *Bacillus amyloliquefaciens* AM0904 deposited as NRRL Deposit Number B-50914, a strain having all of the identifying characteristics of *Bacillus amyloliquefaciens* AM0904 deposited as NRRL Deposit Number B-50914 or a mutant thereof,
   ii) *Bacillus amyloliquefaciens* NP122 deposited as NRRL Deposit Number B-50910, a strain having all of the identifying characteristics of *Bacillus amyloliquefaciens* NP122 deposited as NRRL Deposit Number B-50910 or a mutant thereof, and
   iii) *Bacillus amyloliquefaciens* B2 deposited as NRRL Deposit Number B-50908, a strain having all of the identifying characteristics of *Bacillus amyloliquefaciens* B2 deposited as NRRL Deposit Number B-50908 or a mutant thereof.

112. The use of any of items 102-109 or 111, wherein the one or more probiotic(s) comprises one or more lactic acid bacteria selected from the group consisting of
   i) *Pediococcus acidilactici* FM18 deposited as NRRL Deposit Number B-50964,
   ii) *Pediococcus acidilactici* TY036 deposited as NRRL Deposit Number B-50959, and
   iii) *Enterococcus faecium* MFF109 deposited as NRRL Deposit Number B-50960.

113. The use of any of items 102-112, wherein the one or more probiotic(s) comprises one or more lactic acid bacteria selected from the group consisting of
   i) *Pediococcus acidilactici* FM18 deposited as NRRL Deposit Number B-50964, and
   ii) *Pediococcus acidilactici* TY036 deposited as NRRL Deposit Number B-50959, and 114. The use of any of items 102-113, wherein the one or more probiotic(s) comprises one or more *Bacillus* selected from the group consisting of
   i) *Bacillus amyloliquefaciens* AM0904 deposited as NRRL Deposit Number B-50914,
   ii) *Bacillus amyloliquefaciens* NP122 deposited as NRRL Deposit Number B-50910, and
   iii) *Bacillus amyloliquefaciens* B2 deposited as NRRL Deposit Number B-50908.

115. The use of any of items 102-109, 110-112 or 114, wherein the one or more probiotic(s) comprises a 16S rDNA sequence selected from the group consisting of:
   (a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
   (b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
   (c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 3;
(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;
(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and
(f) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

116. The use of any of items 102-115, wherein the one or more probiotic(s) comprises a 16S rDNA sequence selected from the group consisting of:
(a) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 1;
(b) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 2;
(c) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 4;
(d) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 5; and
(e) 16s rDNA having at least 98%, e.g., at least 98.2%, at least 98.4%, at least 98.6%, at least 98.8%, at least 99.0%, at least 99.2%, at least 99.4%, at least 99.5%, at least 99.6%, at least 99.7%, at least 99.8%, at least 99.9% or 100% sequence identity to SEQ ID NO: 6.

117. The use of any of items 102-116, wherein the one or more performance parameter(s) is selected from the group consisting of body weight gain, growth rate, feed conversion rate and overall health.

118. The use of any of items 102-117, wherein the bacterial bloom in the poultry hatcher cabinet is modified or controlled.

119. The use of any of items 102-118, to the extent possible, wherein the bacterial bloom in the poultry hatcher cabinet is modified, controlled or lowered compared to the bacterial bloom in a poultry hatcher cabinet where the method has not been applied.

120. The use of any of items 102-119, wherein the poultry is chickens and/or turkeys.

121. The use of any of items 102-120, wherein the one or more *Bacillus* strains and one or more lactic acid bacteria strains are administered simultaneously.

122. The use of any of items 102-120, wherein the one or more *Bacillus* strains and one or more lactic acid bacteria strains are administered subsequently in any order.

123. The use of any of items 102-120, wherein the one or more *Bacillus* strains and one or more lactic acid bacteria strains are administered subsequently and wherein the one or more *Bacillus* strains is administered before the one or more lactic acid bacteria strains.

124. The use of any of items 102-120, wherein the one or more *Bacillus* strains and one or more lactic acid bacteria strains are administered subsequently and wherein the one or more lactic acid bacteria strains is administered before the one or more *Bacillus* strains.

125. The use of any of items 102-120, wherein the one or more *Bacillus* strains and one or more lactic acid bacteria strains are administered in successive steps and wherein the one or more *Bacillus* strains is administered before the one or more lactic acid bacteria strains.

126. The use of any of items 102-120, wherein the one or more *Bacillus* strains and one or more lactic acid bacteria strains are administered in successive steps and wherein the one or more lactic acid bacteria strains is administered before the one or more *Bacillus* strains.

127. The use of any of items 102-126, wherein the one or more *Bacillus* strains is administered as a dry formulation.

128. The use of any of items 102-127, wherein the one or more *Bacillus* strains is administered as a wet formulation such as an aqueous formulation.

129. The use of any of items 102-127, wherein the one or more lactic acid bacteria strains is administered as a dry formulation.

130. The use of any of items 102-129, wherein the one or more lactic acid bacteria strains is administered as a wet formulation such as an aqueous formulation.

131. The use of any of items 102-129, wherein the one or more *Bacillus* strains is administered more than once such as 2, 3, 4, 5, 6, 7 8, 9, 10 or more than 10 times.

132. The use of any of items 102-130, wherein the one or more lactic acid bacteria strains is administered more than once such as 2, 3, 4, 5, 6, 7 8, 9, 10 or more than 10 times.

133. The use of any of items 102-132, wherein the one or more *Bacillus* strains is administered in a dose selected from the group consisting of $1 \times 10^5$ to $1 \times 10^6$ CFU *Bacillus* per bird, $1 \times 10^6$ to $1 \times 10^7$ CFU *Bacillus* per bird, $1 \times 10^7$ to $1 \times 10^8$ CFU *Bacillus* per bird, $1 \times 10^8$ to $1 \times 10^9$ CFU *Bacillus* per bird, $1 \times 10^9$ to $1 \times 10^{10}$ CFU *Bacillus* per bird, $1 \times 10^{10}$ to $1 \times 10^{11}$ CFU *Bacillus* per bird, $1 \times 10^{11}$ to $1 \times 10^{12}$ CFU *Bacillus* per bird, or any combination thereof.

134. The use of any of items 102-133, wherein the one or more lactic acid bacteria strains is administered in a dose selected from the group consisting of $1 \times 10^4$ to $1 \times 10^5$ CFU lactic acid bacteria per bird, $1 \times 10^5$ to $1 \times 10^6$ CFU lactic acid bacteria per bird, $1 \times 10^6$ to $1 \times 10^7$ CFU lactic acid bacteria per bird, $1 \times 10^7$ to $1 \times 10^8$ CFU lactic acid bacteria per bird, $1 \times 10^9$ to $1 \times 10^{10}$ CFU lactic acid bacteria per bird, $1 \times 10^{10}$ to $1 \times 10^{11}$ CFU lactic acid bacteria per bird, $1 \times 10^{11}$ to $1 \times 10^{12}$ CFU lactic acid bacteria per bird, or any combination thereof.

135. The use of any of items 102-134, wherein the one or more *Bacillus* and/or the one or more lactic acid bacteria strains is administered at the time of transfer to the hatcher cabinet.

136. The use of any of items 102-135, wherein the one or more *Bacillus* and/or the one or more lactic acid bacteria strains is administered at a time selected from the group consisting of from 10% pip to 20% pip, from 20% pip to 30% pip, from 30% pip to 40% pip, from 40% pip to 50% pip, from 50% pip to 60% pip, from 60% pip to 70% pip, from 70% pip to 80% pip, from 80% pip to 90% pip, from 90% pip to 100% pip, or any combination thereof.

137. The use of any of items 102-136, wherein the one or more *Bacillus* and/or the one or more lactic acid bacteria strains is administered at a time selected from the group consisting of from 10% hatch to 20% hatch, from 20% hatch to 30% hatch, from 30% hatch to 40% hatch, from 40% hatch to 50% hatch, from 50% hatch to 60% hatch, from 60% hatch to 70% hatch, from 70% hatch to 80% hatch, from 80% hatch to 90% hatch, from 90% hatch to 100% hatch, or any combination thereof.

EXAMPLES

Identification, Characterization and Deposit of the Biological Material

The following biological materials were deposited under the terms of the Budapest Treaty at Agricultural Research Service Culture Collection (NRRL), 1815 North University Street, Peoria, Ill. 61604, U.S.A., and given the following accession numbers:

| Identification | Accession Number | Date of Deposit |
| --- | --- | --- |
| Pediococcus acidilactici TY036 | NRRL B-50959 | Apr. 1, 2014 |
| Pediococcus acidilactici FM18 | NRRL B-50964 | Apr. 1, 2014 |
| Enterococcus faecium MFF109 | NRRL B-50960 | Apr. 1, 2014 |
| Bacillus amyloliquefaciens AM0904 | NRRL B-50914 | Mar. 7, 2014 |
| Bacillus amyloliquefaciens NP122 | NRRL B-50910 | Mar. 7, 2014 |
| Bacillus amyloliquefaciens B2 | NRRL B-50908 | Mar. 7, 2014 |

The strains have been deposited under conditions that assure that access to the culture will be available during the pendency of this patent application to one determined by foreign patent laws to be entitled thereto. The deposits represent a substantially pure culture of the deposited strain. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Description of the Biological Material

Pediococcus acidilactici TY036 was isolated from poultry in the US by Pacific Vet Group USA Inc. in 2013. Pediococcus acidilactici FM18 was isolated from poultry in the US by the University of Arkansas in 2003. Enterococcus faecium MFF109 was isolated from poultry in the US by Pacific Vet Group USA Inc. in 2013. Bacillus amyloliquefaciens AM0904 was isolated from poultry in the US by the University of Arkansas in 2009. Bacillus amyloliquefaciens NP122 was isolated from poultry in the US by the University of Arkansas in 2008. Bacillus amyloliquefaciens B2 was isolated from poultry in the US by the University of Arkansas in 2009.

Example 1

Probiotic Bacterial Isolate Screening

Candidate bacterial isolates were previously screened for probiotic potential. The Bacillus had previously been shown to be able to grow rabidly and robustly on minimal media. These strains have also shown the ability to inhibit pathogens both in vitro and in vivo. The lactic acid bacterial isolate FM18 has previously been shown to inhibit Salmonella and Clostridium perfringens both in vitro and in vivo. Lactic acid bacteria strains TY036 and MFF109 had previously been shown to stimulate early gut development in neonatal poultry.

In vitro Test Against Common Poultry Pathogens.

Bacillus isolates (AM0904, NP122, and B2) were incubated on agar plates with Salmonella enteritidis, Salmonella typhimurium, Salmonella heidelberg, Salmonella kentucky, Clostridium perfringens and Escherichia coli and the zone of inhibition was determined.

Lactic acid bacteria isolates (FM18 and TY036) were incubated on agar plates with Salmonella Enteritidis, Salmonella Typhimurium, Salmonella Heidelberg, Salmonella Kentucky, Clostridium perfringens and Escherichia coli and the zone of inhibition was determined Table 1.

TABLE 1

| In vitro Overlay Test Against Common Pathogens | | | | | | |
| --- | --- | --- | --- | --- | --- | --- |
| | Salmonella Enteriditis | Salmonella Typhimurium | Salmonella Heidelberg | Salmonella Kentucky | E. coli F18 | Closridium perfringens |
| AM0904 | +++ | ++ | +++ | +++ | ++ | ++ |
| B2 | ++ | ++ | +++ | +++ | + | ++ |
| NP122 | + | + | − | + | ++ | ++ |
| FM18 | ++++ | ++++ | +++ | ++++ | ++++ | ++++ |
| TY036 | ++++ | +++ | +++ | ++++ | +++ | +++ |
| MFF109 | ++++ | +++ | +++ | ++++ | +++ | +++ |

Briefly, the LAB isolates were grown in de Man, Rogosa and Sharpe (MRS) broth overnight while being incubated at 37° C. The Bacillus were grown in tryptic soy broth overnight while being incubated at 37° C. A sterile loop was used to transfer the LAB onto an MRS plate or the Bacillus onto a tryptic soy agar plate so that a single dense colony will grow on the center of a plate or bi-plate. This plate was incubated for 48 hours at 37° C. for the LAB or 24 hours for the Bacillus. During incubation an overnight culture of the pathogen of interest was incubated in appropriate media at 37° C. 100 microliters of the pathogen culture was added to 10 ml of tryptic soy soft agar held at 45° C. The tryptic soy soft agar was poured over the MRS/tryptic soy agar plate containing the LAB/Bacillus isolate and incubated overnight at 37° C.

Example 2

Testing of Bacterial Formulation in the Hatcher for Environmental Control of Pathogenic Bacteria Experiment 1

Figure 3:
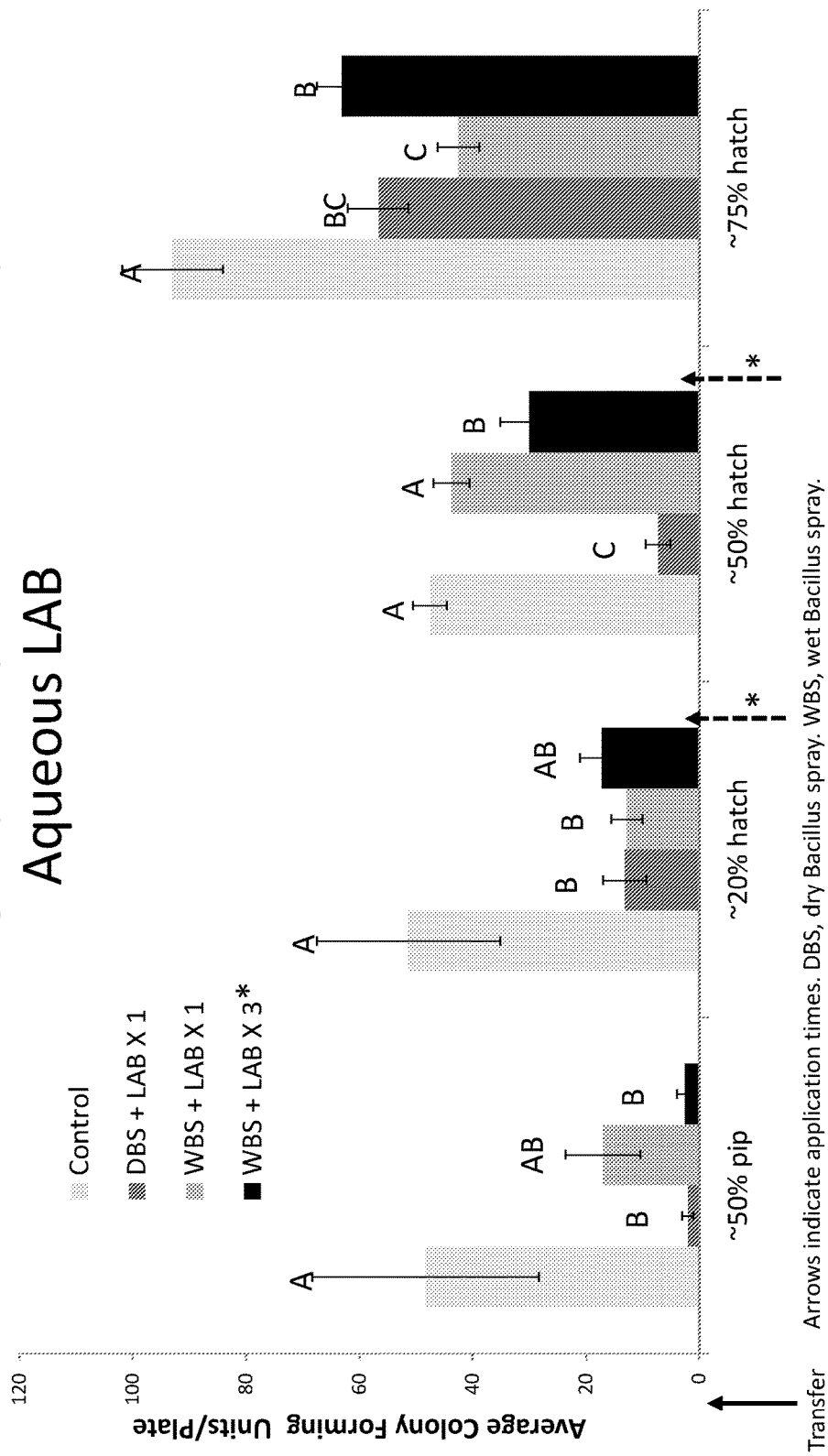
FIG. 3 illustrates amount of gram negative/coliform bacteria present in hatcher post administration of bacterial formulation in experiment 1.

Several test formulations were evaluated for effect within commercial hatchers and measured against a control hatcher. Commercial breeder flocks were stratified so that incoming bacterial load was a controlled factor. All hatchers were in a common hatcher hall. Control hatcher was not treated with probiotic or chemicals. The treatment groups were as follows: 1) negative control 2) single dose of dry bacillus spores (DBS) plus aqueous lactic acid bacteria solution (LAB) 3) single application of aqueous bacillus spores (WBS) plus LAB 4) 3 applications of WBS and LAB. All applications were performed using a hand held pneumatic sprayer. The single treatments were given at transfer. The three application groups were treated at transfer, 20% hatch, and 50% hatch. Each dose of DBS was approximately $3 \times 10^8$ spores per bird per application. Each dose of WBS was approximately $3 \times 10^8$ spores per bird per application. Each dose of LAB was approximately $3 \times 10^6$ cfu per bird per application. The dry *Bacillus* spores were produced separately in a solid state media, dried, ground, then enumerated. The wet Bacillus spores were grown separately in a broth fermentation, centrifuged, lyophilized, ground, and then enumerated. The spores were given in a 5:5:1 ratio of NP122:B2:AM0904 respectively. The lactic acid bacteria (TY036, MFF109, and FM18) were grown separately in a broth fermentation, centrifuged, lyophilized, ground, and then enumerated. Each strain was included in equal amounts. To measure non-selective recovery, 6 plates of tryptic soy agar were placed into the hatchers for a period of 5 minutes at each of the following points: transfer, 50% pip, 20% hatch, 50% hatch, and 75% hatch. To measure gram negative bacteria, 6 plates of MacConkey agar were placed into the hatchers for a period of 5 minutes at each of the following points: transfer, 50% pip, 20% hatch, 50% hatch, and 75% hatch. To measure lactic acid bacteria, 6 plates of Regosa agar were placed into the hatchers for a period of 5 minutes at each of the following points: transfer, 50% pip, 20% hatch, 50% hatch, and 75% hatch. For all plate types, the plates were incubated for 24 hours at 37° C. The single dose of dry bacillus proved to give a higher aerobic bacteria count at all time points FIG. 1. Visually, the predominant colony morphology on these plates were *Bacillus*. Lactic acid bacteria counts were low at all time points for control and single dose. LAB groups at all time points FIG. 2. LAB was increased at the 50% hatch and 75% hatch time points. Gram negative recovery was lower in the treatment groups at three of the four time points measured FIG. 3. These results indicate that dry *Bacillus* spores persist longer than aqueous *Bacillus* in the hatcher. These results also indicate that LAB do not persist in the hatcher for a long period of time. Because of this multiple doses of LAB are needed. All treatments significantly reduced gram negatives. This indicates that these formulations are potential candidates to reduce the pathogenic bloom of bacteria (i.e. bacterial bloom) within the hatcher cabinet.

Experiment 2

Figure 4:
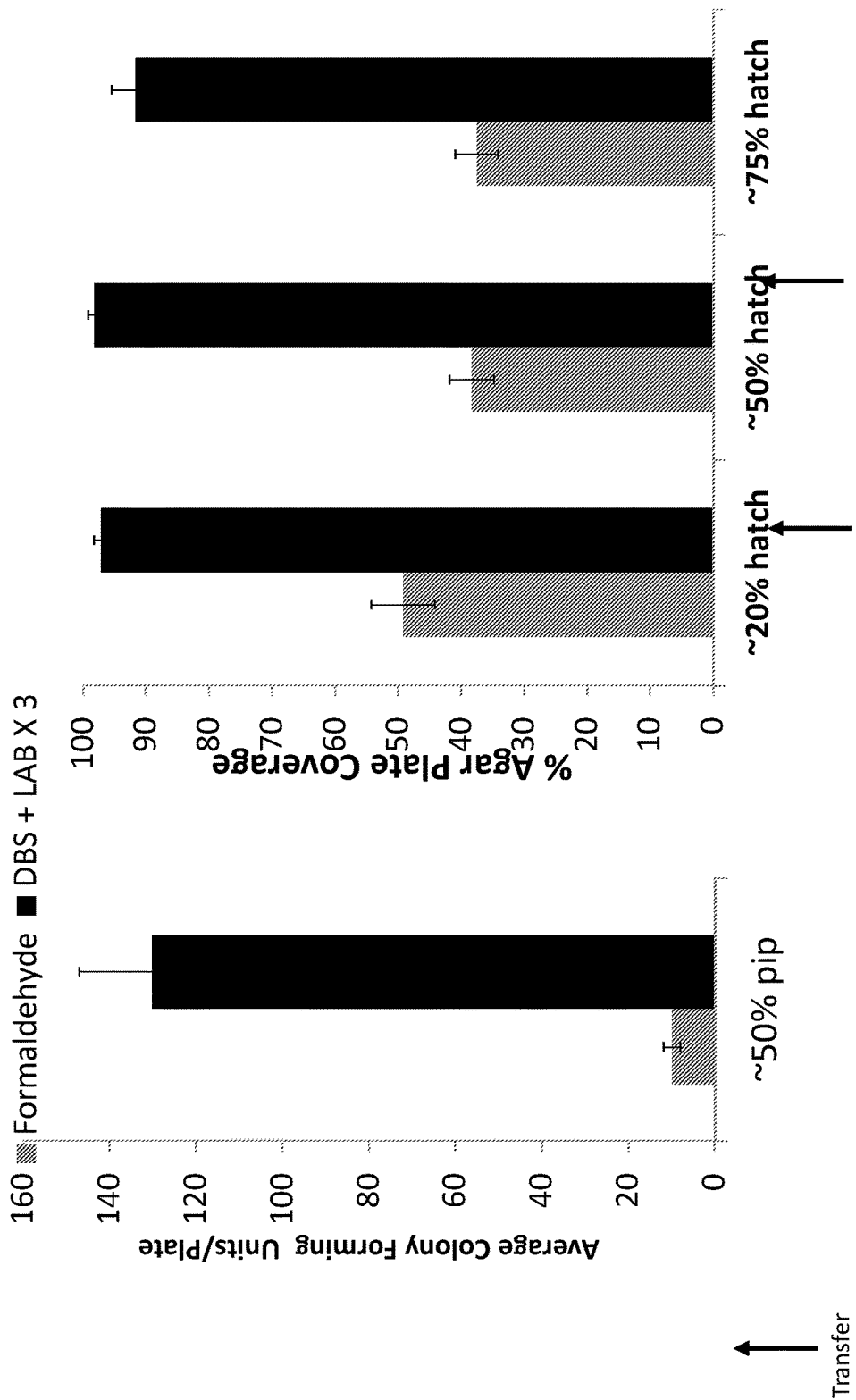
FIG. 4 illustrates evaluation of general bacteria and combinations of lactic acid bacteria isolates on poultry pathogen reduction in an in vitro overlay assay.
Figure 5:
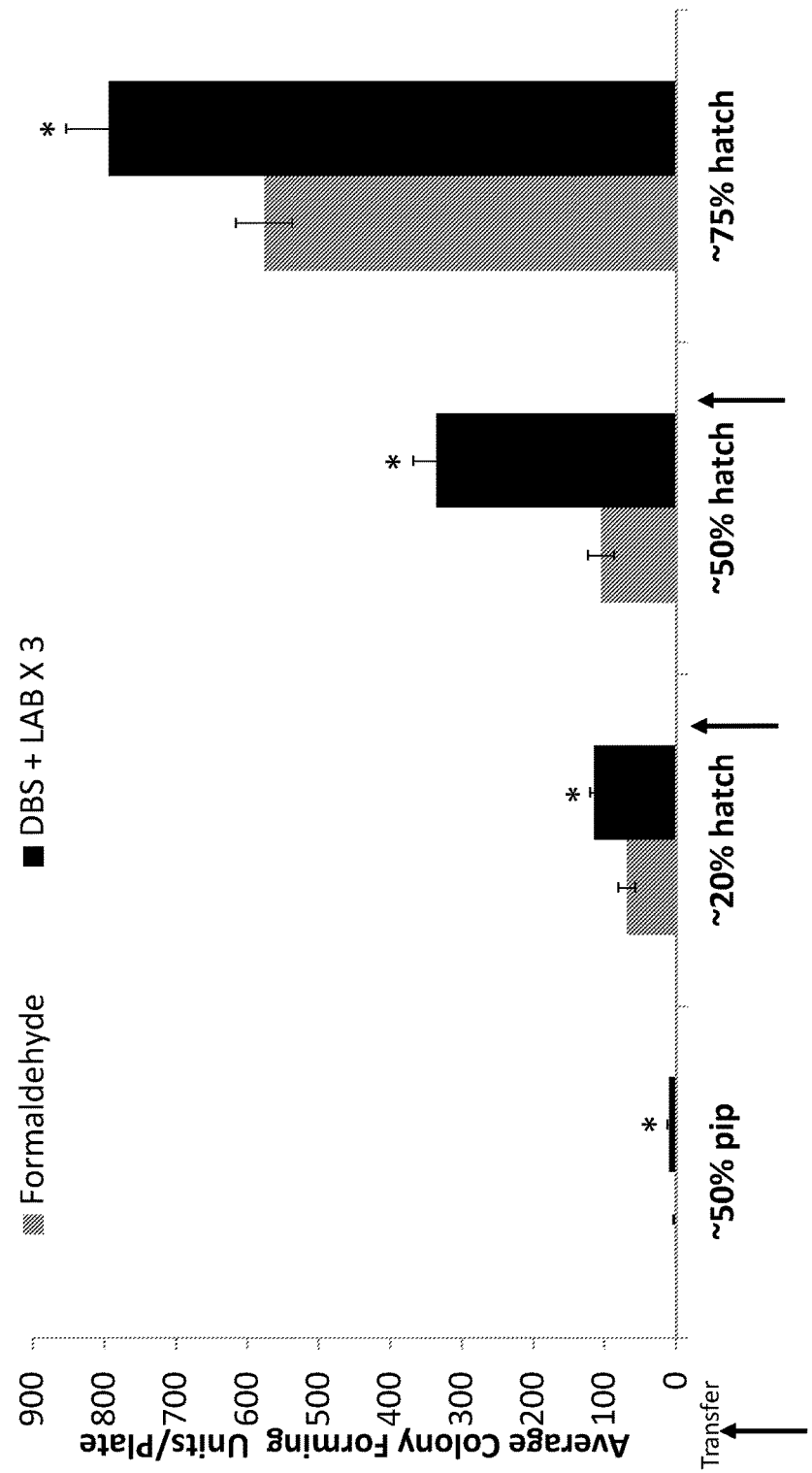
FIG. 5 illustrates amount of lactic acid bacteria present in hatcher post administration of bacterial formulation in experiment 2.
Figure 6:
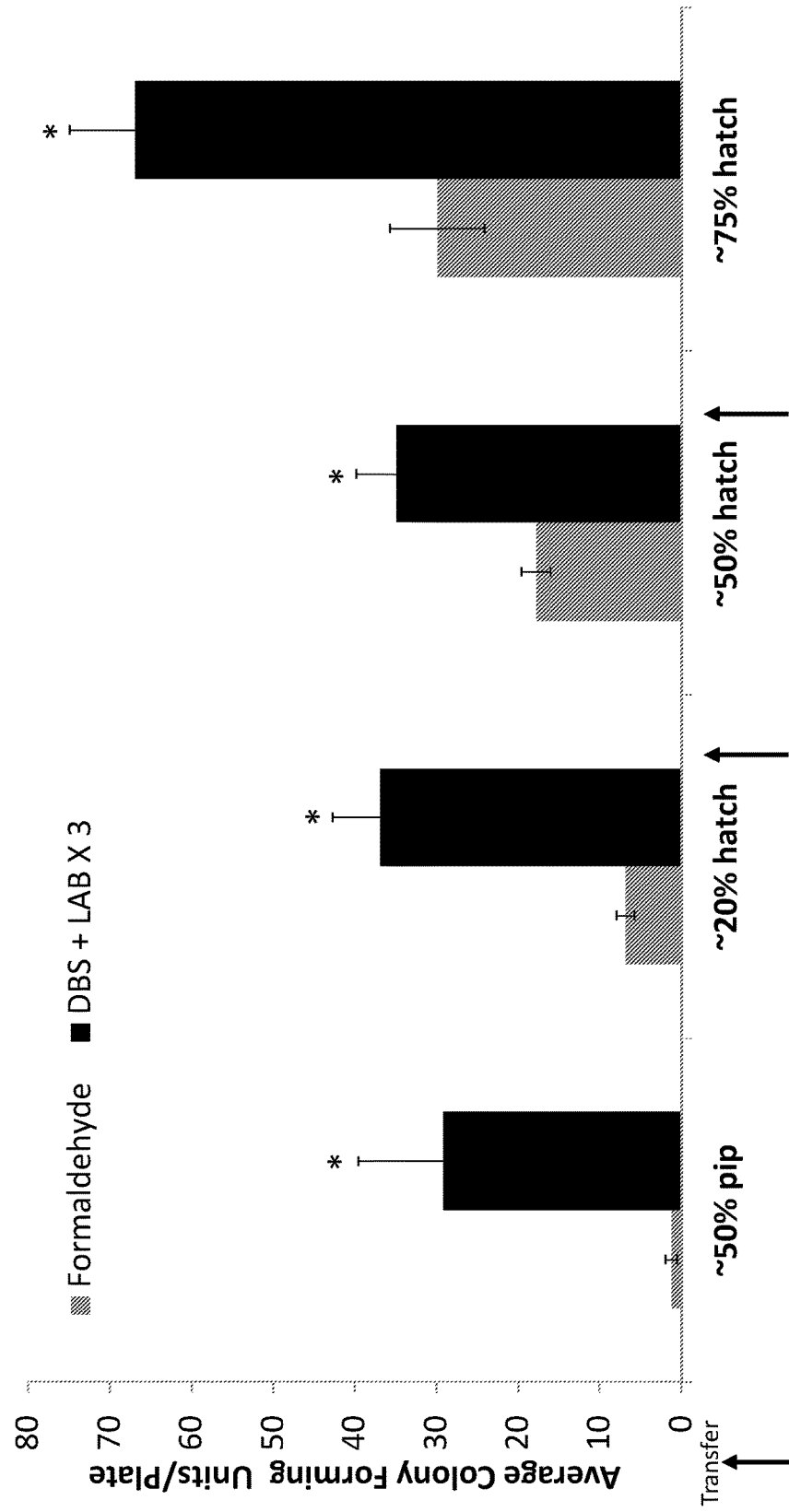
FIG. 6 illustrates amount of gram negative/coliform bacteria present in hatcher post administration of bacterial formulation in experiment 2.

A test formulation was evaluated for effect within hatchers and measured against control hatchers. Breeder flocks were stratified so that incoming bacterial load was a controlled factor. All hatchers were in a common hatcher hall and were of the same type. Control hatcher was not treated with probiotic but was treated with formaldehyde. The treatment group was three applications of dry bacillus spores (DBS) plus three doses of aqueous lactic acid bacteria solution and was compared to control (formaldehyde treated) hatchers. The *Bacillus* spores were produced separately in a solid state media, dried, ground, then enumerated. The spores were given in a 5:5:1 ratio of NP122:B2: AM0904 respectively. The lactic acid bacteria (TY036, MFF109, and FM18) were grown separately in a broth fermentation, centrifuged, lyophilized, ground, and then enumerated. Each strain was included in equal amounts. The three doses supplied $1 \times 10^9$ spores per bird and $1 \times 10^7$ cfu of lactic acid bacteria per bird over the treatment period. To measure non-selective recovery, 6 plates of tryptic soy agar were placed into the hatchers for a period of 5 minutes at each of the following points: transfer, 50% pip, 20% hatch, 50% hatch, and 75% hatch. To measure gram negative bacteria, 6 plates of MacConkey agar were placed into the hatchers for a period of 5 minutes at each of the following points: transfer, 50% pip, 20% hatch, 50% hatch, and 75% hatch. To measure lactic acid bacteria, 6 plates of MRS agar were placed into the hatchers for a period of 5 minutes at each of the following points: transfer, 50% pip, 20% hatch, 50% hatch, and 75% hatch. For all plate types, the plates were incubated for 24 hours at 37° C. The treatments were given at transfer, 20% hatch, and 50% hatch. Total aerobic plate counts were higher at all time points FIG. 4. The predominant colony morphology of the treated group was *Bacillus*. Lactic acid bacteria counts were also higher at all time points FIG. 5. Gram negative bacteria were also higher at all time points in the treated hatchers FIG. 6. These results indicate that the beneficial bacteria supplied by the formulation were present and in higher amounts in the treated as compared to the control groups. While the amount of gram negative bacteria was also higher in the treatment groups, the increase was less than 0.5 log10 cfu. This was compared to a harsh chemical, formaldehyde. This indicates that this formulation may be an effective alternative to formaldehyde at reducing the bacterial bloom within the hatcher cabinet.

Example 3

Figure 7:
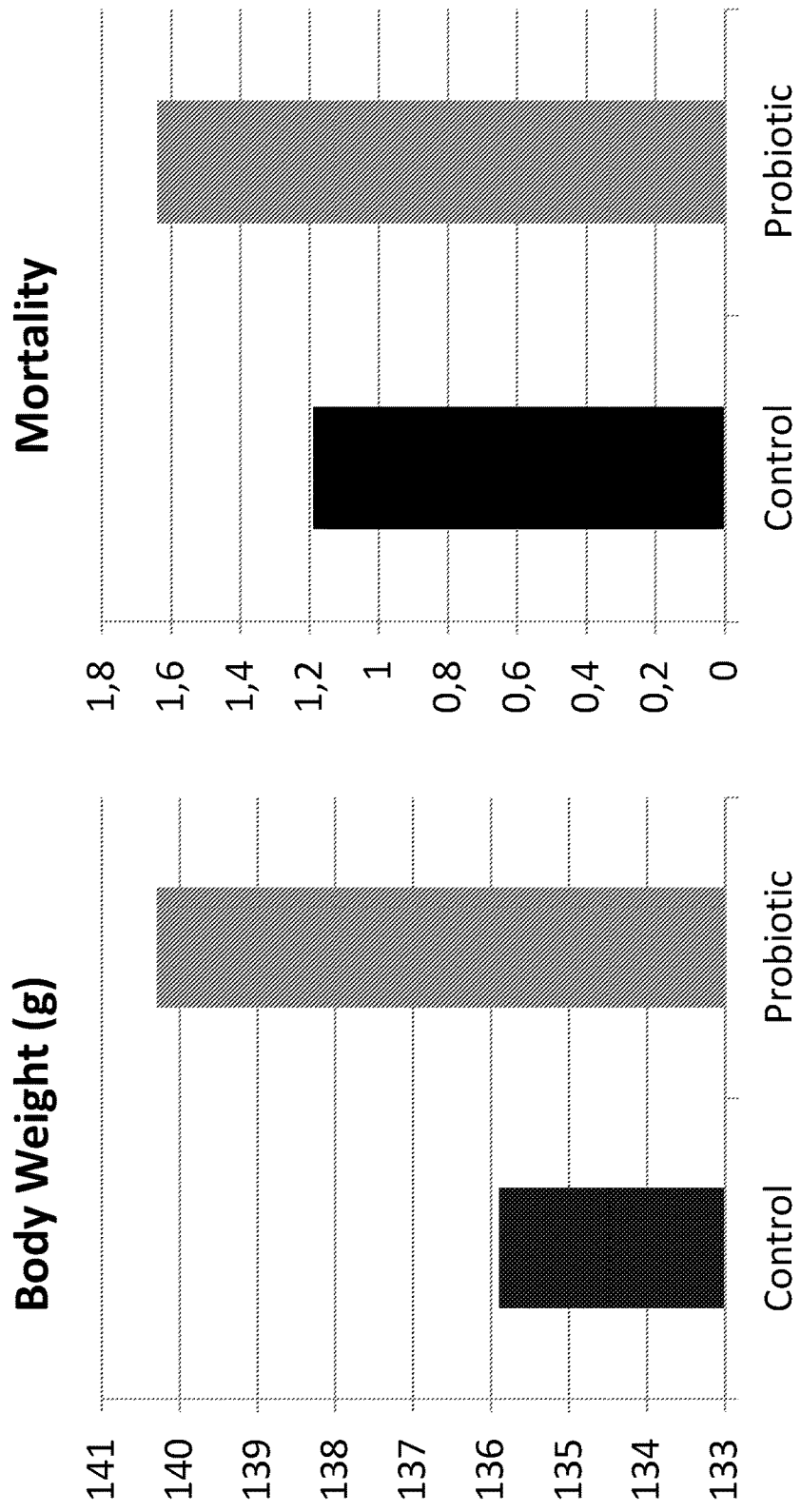
FIG. 7 illustrates impact of the bacterial formulation on 7 day body weight and mortality on broiler chicks experiment 3.
Figure 8:
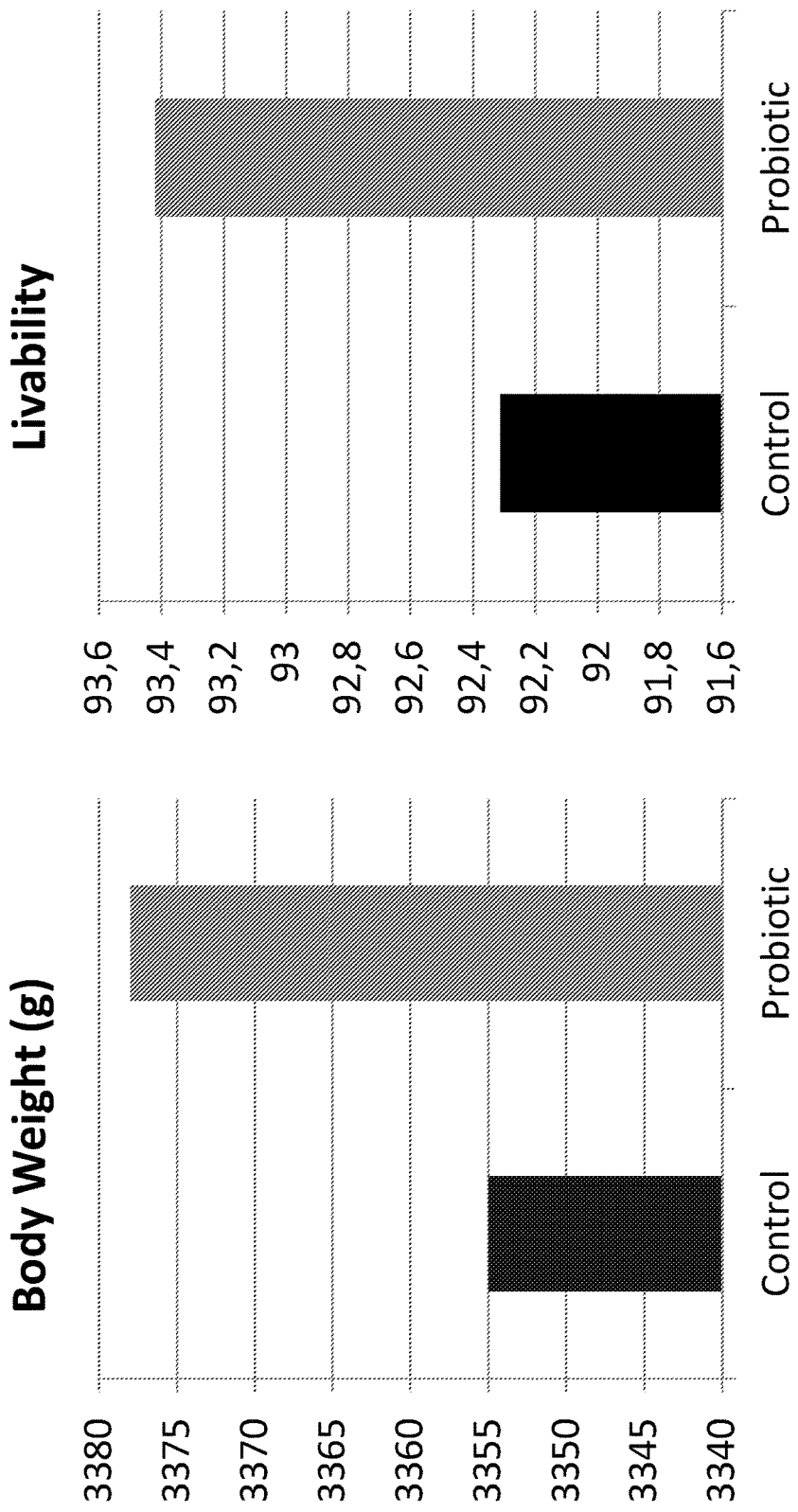
FIG. 8 illustrates impact of the bacterial formulation on body weight and livability of broiler chickens at sale in a commercial environment experiment 3.
Figure 9:
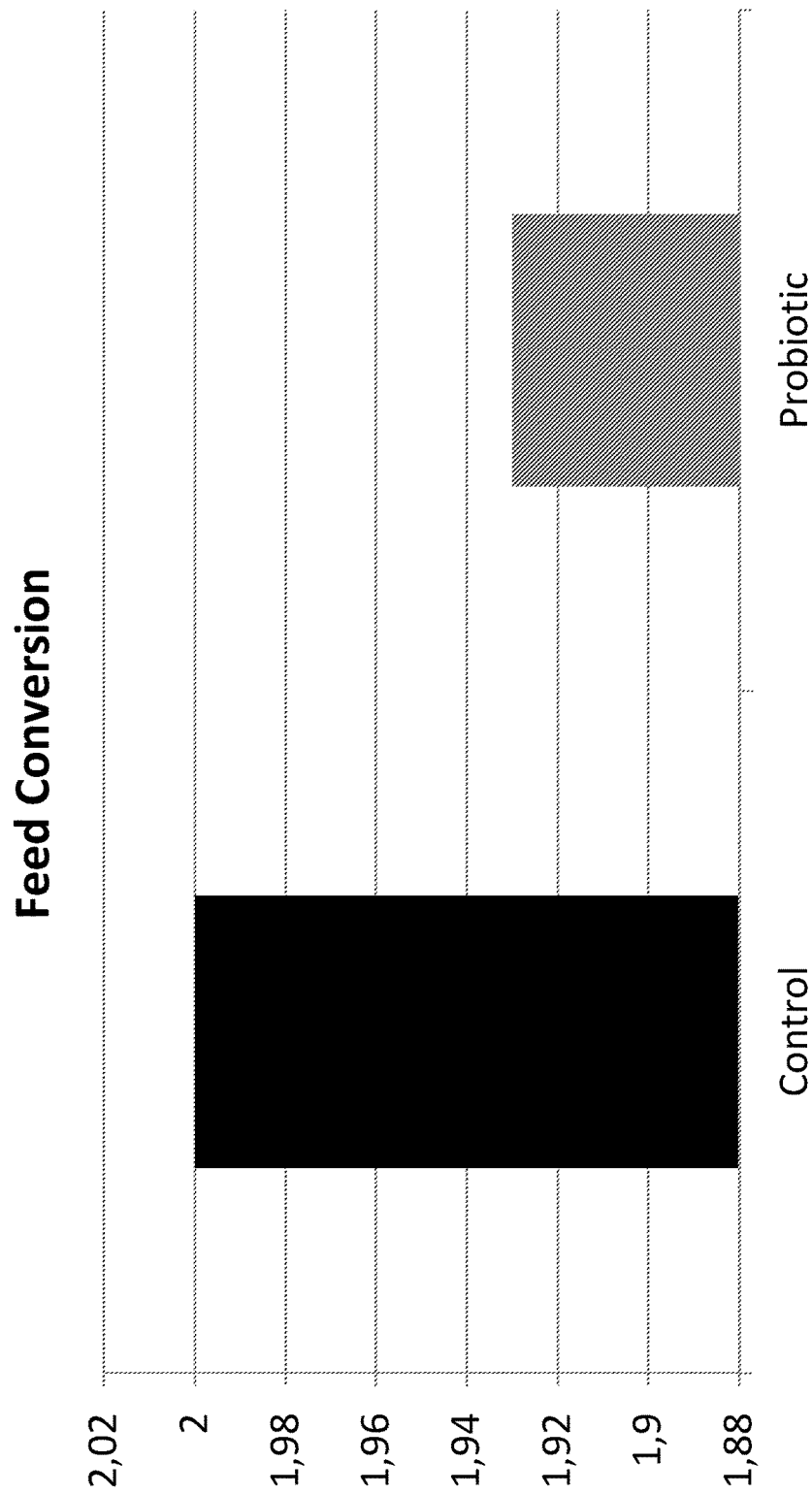
FIG. 9 illustrates impact of the bacterial formulation on feed conversion of broiler chickens at sale in a commercial environment experiment 3.

Testing of Bacterial Formulation for Performance Improvements in Broiler Chickens The bacterial formulation, comprised of three *Bacillius* isolates (AM0904,N P122), in a dry powder formulation were combined with three strains of lactic acid bacteria (FM18, TY036, and MFF109) also in a dry powder form. The formulation was administered at transfer, 20% hatch, and 50% hatch, and 75% hatch via a mechanical pneumatic dispenser. The four doses supplied $1 \times 10^9$ spores per bird and $1 \times 10^7$ cfu of lactic acid bacteria per bird over the treatment period. The *Bacillus* spores were produced separately in a solid state media, dried, ground, then enumerated. The spores were given in a 5:5:1 ratio of NP122:B2:AM0904 respectively. The lactic acid bacteria (TY036, MFF109, and FM18) were grown separately in a broth fermentation, centrifuged, lyophilized, ground, and them enumerated. Each strain was included in equal amounts. The powder was applied into the ventilation system of the hatcher and the stir fans were used to distribute the beneficial bacteria from the formulation around the hatcher cabinet. Breeder flocks were randomized between the treated and control groups to control for incoming bacterial load and egg size. A single hatcher hallway was divided between control and treated groups to control for hatcher environment. Further contract commercial farms were divided between control and treated groups to control for growout house(barn) environment and management. A total 16 houses (400,000 broilers) were evaluated (8 treated and 8 control houses). Seven day body weights and mortality were measured. In each house, treated or control, at least 400 chicks were weighed in 10 bird lots. Chicks were taken from different points within the house to reduce sampling error. Seven day mortality was taken from records maintained for wach barn by the flock manager. Treated groups had improved 7 day body weight and improved 7 day mortality FIG. 7. Body weight and livability at sale of the flocks were also improved in the treatment groups FIG. 8. Feed conversion of the treated flocks was 7 points higher FIG. 9. End of flocks data was reported by the broiler integrator using their methods of data collection. These results indicate that the bacterial formulation improved performance at both 7 days at the end of the flock. Body weight and livability showed continued divergence from 7 days to the end of the flock. The 7 points of feed conversion improvement showed a 3.5% improvement utilization of feed, the major cost of growing broilers and an indicator of flock health and performance.

Example 4

Testing of Bacterial Formulation Treated Chicks for Thermotolerant Spores, Presumptive Lactic Acid Bacteria (LAB) and Gram-Negative Bacteria Guts from chicks treated with either the bacterial formulation of example 3 or formaldehyde were tested for thermotolerant spores, presumptive Lactic Acid Bacteria (LAB) and Gram-negative bacteria.

Materials and Methods

Directly prior to chick removal from the hatchers twelve birds per treatment group were removed from the hatcher. Birds were transported (~1 h) to an appropriate research facility and humanely euthanized by $CO_2$ asphyxiation. Gut packs containing duodenum, ileum, and ceca were aseptically removed and separately homogenized. Gut samples were diluted in sterile saline at a 1:4 wt/vol rate. Ten-fold dilutions were made by placing 200 μl of the sample (N) into the first row of a sterile 96-well plate and sequentially diluting by transferring 20 μl to 180 μl sterile saline to the $10^{-7}$ dilution. The dilutions (N to $10^{-7}$) were plated by 10 μl drop onto both MRS agar and MacConkey's agar. For Trypticase soy agar (TSA) plating, the gut samples were Pasteurized at 80° C. for 10 min before transferring 200 μl into a 96 well plate. The rest of the dilutions and plating methods were the same as the MRS and MacConkey's agar. Agar plates were counted after 24 h of incubation at 37° C.

Results and Discussion

A marked increase in thermotolerant spores was found in the GIT of chicks treated with the bacterial formulation as shown in table 2. The abnormally high counts in Exp 1 were due to the samples not being pasteurized prior to dilution and plating. Subsequent experiments included a pasteurization step.

TABLE 2

Average enumeration ($Log_{10}$ CFU/g) of thermotolerant spore counts in day of hatch (DOH) commercial broiler chicks. Averages are based on n = 12 and shown with ± Std Err. Tryptic Soy Agar (TSA) (Pasteurized; Spore count)

| Treatment Group | Exp 1 | Exp 2 | Exp 3 | Exp 4 | Exp 5 |
|---|---|---|---|---|---|
| Formaldehyde | 8.95 ± 0.2 | 1.34 ± 0.48 | 0.69 ± 0.36 | 0.44 ± 0.3 | 0 ± 0 |
| Bacterial formulation | 8.22 ± 0.4 | 5.3 ± 0.15* | 5.83 ± 0.18* | 5.01 ± 0.17* | 5.37 ± 0.17* |

*denotes significant difference (p < 0.05) between formaldehyde and bacterial formulation groups The number of presumptive Lactic Acid Bacteria (LAB) isolated from the GIT of chicks treated with either formaldehyde or the bacterial formulation were counted and are shown in table 3. With the exception of Exp 5, all experiments showed a decrease in the number of LABs recovered from the chick GIT compared to formaldehyde treated chicks. One hypothesis for this observation is that the two *Pedicoccus acidilactici* strains in the bacterial formulation product were selected to outcompete other LAB isolates and may be inhibiting the growth and colonization of other wild-type LABs, reducing the overall number of LABs present. This trend was not seen in Exp 5, though the unusually low number of LABs seen in the formaldehyde group likely contributed to this result.

TABLE 3

Average enumeration ($Log_{10}$ CFU/g) of presumptive Lactic Acid bacteria counts in DOH commercial broiler chicks. Averages are based on n = 12 and shown with ± Std Err. Mann-Rogosa-Sharp (MRS) Agar (Presumptive LAB count)

| Treatment Group | Exp 1 | Exp 2 | Exp 3 | Exp 4 | Exp 5 |
|---|---|---|---|---|---|
| Formaldehyde | 7.79 ± 0.17 | 7.26 ± 0.34 | 6.26 ± 0.83 | 5.1 ± 0.99 | 2.85 ± 0.96 |
| Bacterial formulation | 6.77 ± 0.56 | 2.88 ± 0.79* | 4.64 ± 0.78 | 3.86 ± 0.93 | 4.82 ± 0.77 |

*denotes significant difference (p < 0.05) between formaldehyde and bacterial formulation groups The number of Gram-negative bacteria, which are considered to be either pathogenic or non-beneficial to the host, were isolated is shown in Table 4. In all but Exp 5, the number of Gram-negative bacteria was shown to be lower in the bacterial formulation-treated birds than the formaldehyde treated chicks. All of the probiotic isolates in the bacterial formulation have been shown to have an inhibitory effect against common Gram-negative isolates. In Exp 5 the Gram-negative bacteria counts were the same between the formaldehyde and the bacterial formulation groups, though the overall numbers for both groups were very low. It is likely that the bacterial formulation is only capable of reducing Gram-negative bacteria numbers down to a certain level, as very low levels result in low bacterial densities in the gut, making it less likely that the bacterial formulation isolates and Gram-negative bacteria will be in direct competition.

TABLE 4

Average enumeration ($Log_{10}$ CFU/g) of presumptive Gram-negative bacteria counts in DOH commercial broiler chicks. Averages are based on n = 12 and shown with ± Std Err. MacConkey's agar (Gram-negative count)

| Treatment Group | Exp 1 | Exp 2 | Exp 3 | Exp 4 | Exp 5 |
| --- | --- | --- | --- | --- | --- |
| Formaldehyde | 8.39 ± 0.19 | 6.56 ± 0.83 | 3.9 ± 0.93 | 4.95 ± 0.99 | 2.84 ± 0.92 |
| Bacterial formulation | 5.79 ± 0.91* | 2.6 ± 0.83* | 1.32 ± 0.7* | 3.14 ± 1.02 | 2.95 ± 1.1 |

*denotes significant difference ($p < 0.05$) between formaldehyde and bacterial formulation groups

The invention claimed is:

1. A composition comprising a silicate flow aid, one or more *Bacillus* strains and one or more lactic acid bacteria strains, wherein:
   the one or more *Bacillus* strains comprise one or more of *Bacillus amyloliquefaciens* AM0904, *Bacillus amyloliquefaciens* NP122 and *Bacillus amyloliquefaciens* B2, and/or
   the one or more lactic acid bacteria strains comprise one or more of *Pediococcus acidilactici* FM18, *Pediococcus acidilactici* TY036 and *Enterococcus faecium* MFF109.

2. The composition of claim 1, comprising one or more of *Bacillus amyloliquefaciens* AM0904, *Bacillus amyloliquefaciens* NP122 and *Bacillus amyloliquefaciens* B2.

3. The composition of claim 1, comprising one or more of *Pediococcus acidilactici* FM18, *Pediococcus acidilactici* TY036 and *Enterococcus faecium* MFF109.

4. The composition of claim 1, comprising:
   one or more of *Bacillus amyloliquefaciens* AM0904, *Bacillus amyloliquefaciens* NP122 and *Bacillus amyloliquefaciens* B2, and
   one or more of *Pediococcus acidilactici* FM18, *Pediococcus acidilactici* TY036 and *Enterococcus faecium* MFF109.

5. The composition of claim 1, comprising at least two of *Bacillus amyloliquefaciens* AM0904, *Bacillus amyloliquefaciens* NP122 and *Bacillus amyloliquefaciens* B2.

6. The composition of claim 1, comprising at least two of *Pediococcus acidilactici* FM18, *Pediococcus acidilactici* TY036 and *Enterococcus faecium* MFF109.

7. The composition of claim 1, comprising:
   at least two of *Bacillus amyloliquefaciens* AM0904, *Bacillus amyloliquefaciens* NP122 and *Bacillus amyloliquefaciens* B2, and
   at least two of *Pediococcus acidilactici* FM18, *Pediococcus acidilactici* TY036 and *Enterococcus faecium* MFF109.

8. The composition of claim 1, comprising *Bacillus amyloliquefaciens* AM0904, *Bacillus amyloliquefaciens* NP122 and *Bacillus amyloliquefaciens* B2.

9. The composition of claim 1, comprising *Pediococcus acidilactici* FM18, *Pediococcus acidilactici* TY036 and *Enterococcus faecium* MFF109.

10. The composition of claim 1, comprising *Bacillus amyloliquefaciens* AM0904, *Bacillus amyloliquefaciens* NP 122, *Bacillus amyloliquefaciens* B2, *Pediococcus acidilactici* FM18, *Pediococcus acidilactici* TY036 and *Enterococcus faecium* MFF109.

11. The composition of claim 1, wherein said composition is a powder formulation.

12. A method comprising contacting a poultry egg with the composition of claim 1.

13. A method comprising contacting a poultry egg with the composition of claim 4.

14. A method comprising contacting a poultry egg with the composition of claim 7.

15. A method comprising contacting a poultry egg with the composition of claim 10.

16. A method comprising introducing the composition of claim 1 into a poultry hatcher cabinet.

17. A method comprising introducing the composition of claim 4 into a poultry hatcher cabinet.

18. A method comprising introducing the composition of claim 7 into a poultry hatcher cabinet.

19. A method comprising introducing the composition of claim 10 into a poultry hatcher cabinet.

20. A method comprising contacting a poultry egg and/or a poultry hatcher cabinet with a powder formulation comprising a silicate flow aid, *Bacillus amyloliquefaciens* AM0904, *Bacillus amyloliquefaciens* NP122, *Bacillus amyloliquefaciens* B2, *Pediococcus acidilactici* FM18, *Pediococcus acidilactici* TY036 and *Enterococcus faecium* MFF109.

* * * * *

SEQUENCE LISTING

<160> NUMBER OF SEQ ID NOS: 6

<210> SEQ ID NO 1
<211> LENGTH: 1447
<212> TYPE: DNA
<213> ORGANISM: Pediococcus acidilactici

<400> SEQUENCE: 1

```
agacggctag ctcctaaaag gttacccccac cggctttggg tgttacaaac tctcatggtg      60
tgacgggcgg tgtgtacaag gcccgggaac gtattcaccg cggcatgctg atccgcgatt     120
actagcgatt ccgacttcgt gtaggcgagt tgcagcctac agtccgaact gagaatggtt     180
ttaagagatt agctaaacct cgcggtttcg cgactcgttg taccatccat tgtagcacgt     240
gtgtagccca ggtcataagg ggcatgatga tttgacgtcg tccccacctt cctccggttt     300
gtcaccggca gtctcactag agtgcccaac tgaatgctgg caactagtaa taagggttgc     360
gctcgttgcg ggacttaacc caacatctca cgacacgagc tgacgacaac catgcaccac     420
ctgtcattct gtccccgaag ggaacgccta atctcttagg ttggcagaag atgtcaagac     480
ctggtaaggt tcttcgcgta gcttcgaatt aaaccacatg ctccaccgct tgtgcgggcc     540
cccgtcaatt cttttgagtt tcaaccttgc ggtcgtactc cccaggcgga ttacttaatg     600
cgttagctgc agcactgaag ggcggaaacc ctccaacact tagtaatcat cgtttacggc     660
atggactacc agggtatcta atcctgttcg ctacccatgc tttcgagcct cagcgtcagt     720
tacagaccag acagccgcct tcgccactgg tgttcttcca tatatctacg catttcaccg     780
ctacacatgg agttccactg tcctcttctg cactcaagtc tcccagtttc caatgcactt     840
cttcggttga gccgaaggct ttcacattag acttaaaaga ccgcctgcgc tcgctttacg     900
cccaataaat ccggataacg cttgccacct acgtattacc gcggctgctg gcacgtagtt     960
agccgtggct ttctggttaa ataccgtcac tgggtgaaca gttactctca cccacgttct    1020
tctttaacaa cagagcttta cgagccgaaa cccttcttca ctcacgcggc gttgctccat    1080
cagacttgcg tccattgtgg aagattccct actgctgcct cccgtaggag tctgggccgt    1140
gtctcagtcc caatgtggcc gattaccctc tcaggtcggc tacgcatcat cgccttggtg    1200
agccgttacc tcaccaacta gctaatgcgc cgcgggtcca tccagaagtg atagcagagc    1260
```

| | |
|---|---|
| catcttttaa aagaaaacca ggcggttttc tctgttatac ggtattagca tctgtttcca | 1320 |
| ggtgttatcc cctgcttctg gcaggttac ccacgtgtta ctcacccgtc cgccactcac | 1380 |
| ttcgtgttaa aatctcattc agtgcaagca cgtcataatc aattaacgga agttcgttcg | 1440 |
| acttgca | 1447 |

<210> SEQ ID NO 2
<211> LENGTH: 1437
<212> TYPE: DNA
<213> ORGANISM: Pediococcus acidilactici
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (1433)..(1433)
<223> OTHER INFORMATION: n is a, c, g, or t

<400> SEQUENCE: 2

| | |
|---|---|
| ggctagctcc taaaaggnta ccccaccggc tttgggtgtt acaaactctc atggtgtgac | 60 |
| gggcggtgtg tacaaggccc gggaacgtat tcaccgcggc atgctgatcc gcgattacta | 120 |
| gcgattccga cttcgtgtag gcgagttgca gcctacagtc cgaactgaga atggttttaa | 180 |
| gagattagct aaacctcgcg gtttcgcgac tcgttgtacc atccattgta gcacgtgtgt | 240 |
| agcccaggtc ataaggggca tgatgatttg acgtcgtccc caccttcctc cggtttgtca | 300 |
| ccggcagtct cactagagtg cccaactgaa tgctggcaac tagtaataag ggttgcgctc | 360 |
| gttgcgggac ttaacccaac atctcacgac acgagctgac gacaaccatg caccacctgt | 420 |
| cattctgtcc ccgaagggaa cgcctaatct cttaggttgg cagaagatgt caagacctgg | 480 |
| taaggttctt cgcgtagctt cgaattaaac cacatgctcc accgcttgtg cgggcccccg | 540 |
| tcaattcttt tgagtttcaa ccttgcggtc gtactcccca ggcggattac ttaatgcgtt | 600 |
| agctgcagca ctgaagggcg gaaaccctcc aacacttagt aatcatcgtt tacggcatgg | 660 |
| actaccaggg tatctaatcc tgttcgctac ccatgctttc gagcctcagc gtcagttaca | 720 |
| gaccagacag ccgccttcgc cactggtgtt cttccatata tctacgcatt tcaccgctac | 780 |
| acatggagtt ccactgtcct cttctgcact caagtctccc agtttccaat gcacttcttc | 840 |
| ggttgagccg aaggctttca cattagactt aaaagaccgc ctgcgctcgc tttacgccca | 900 |
| ataaatccgg ataacgcttg ccacctacgt attaccgcgg ctgctggcac gtagttagcc | 960 |
| gtggctttct ggttaaatac cgtcactggg tgaacagtta ctctcaccca cgttcttctt | 1020 |
| taacaacaga gctttacgag ccgaaaccct tcttcactca cgcggcgttg ctccatcaga | 1080 |
| cttgcgtcca ttgtggaaga ttccctactg ctgcctcccg taggagtctg ggccgtgtct | 1140 |
| cagtcccaat gtggccgatt accctctcag gtcggctacg catcatcgcc ttggtgagcc | 1200 |
| gttacctcac caactagcta atgcgccgcg gtccatcca gaagtgatag cagagccatc | 1260 |
| ttttaaaaga aaaccaggcg gttttctctg ttatacggta ttagcatctg tttccaggtg | 1320 |
| ttatcccctg cttctgggca ggttaccac gtgttactca cccgtccgcc actcacttcg | 1380 |
| tgttaaaatc tcattcagtg caagcacgtc ataatcaatt aacggaagtt cgntcga | 1437 |

<210> SEQ ID NO 3
<211> LENGTH: 708
<212> TYPE: DNA
<213> ORGANISM: Enterococcus faecium

<400> SEQUENCE: 3

```
tccatatatc tacgcatttc accgtgagct cgcattccac tctcctcttc tgcactcaag      60
tctcccagct ccaatgaccc tccccggttg agccggggc tttcacatca gacttaagaa      120
accgcctgcg ctcgctttac gcccaatcma tccggacaac gcttgccacc tacgtattac     180
cgcggctgct ggcacgtagt tagccgtggc tttctggtta gataccgtca agggatgaac     240
agttactctc atccttgttc ttctctaaca acagagtttt acgatccgaa aaccttcttc     300
actcacgcgg ygttgctcgg tcagactttc gtccattgcc gaagattccc tactgctgcc     360
tcccgtagga gtttgggccg tgtctcagty ccaatgttky cgatcaccct ctcaggtcgg     420
ctatkttwtt ktggccttgg tgagccgtta cctcaccaac tagctaatgc accgcgggtc     480
catccatcag cgacacccga aagcgccttt caaatcaaaa ccatgcggtt tcgattgtta     540
tacggtatta gcacctgttt ccaagtgtta tccccttctg atgggcaggt tacccacgtg     600
ttactcaccc gttcgccact cctcttttc cggtggagca agctccgrtg gaaaagaag       660
cgttcgactt gcatgtatta ggcacgccgc cagcgttcgt cctgagcc                  708
```

<210> SEQ ID NO 4
<211> LENGTH: 1422
<212> TYPE: DNA
<213> ORGANISM: Bacillus amyloliquefaciens
<220> FEATURE:
<221> NAME/KEY: misc_feature
<222> LOCATION: (17)..(17)
<223> OTHER INFORMATION: n is a, c, g, or t

<400> SEQUENCE: 4

```
ttcggcggct ggctccntaa aggttacctc accgacttcg ggtgttacaa actctcgtgg     60
tgtgacgggc ggtgtgtaca aggcccggga acgtattcac cgcggcatgc tgatccgcga     120
ttactagcga ttccagcttc acgcagtcga gttgcagact gcgatccgaa ctgagaacag     180
atttgtggga ttggcttaac ctcgcggttt cgctgccctt tgttctgtcc attgtagcac     240
gtgtgtagcc caggtcataa ggggcatgat gatttgacgt catccccacc ttcctccggt     300
ttgtcaccgg cagtcacctt agagtgccca actgaatgct ggcaactaag atcaagggtt     360
gcgctcgttg cgggacttaa cccaacatct cacgacacga gctgacgaca accatgcacc     420
acctgtcact ctgccccga aggggacgtc ctatctctag gattgtcaga ggatgtcaag     480
acctggtaag gttcttcgcg ttgcttcgaa ttaaaccaca tgctccaccg cttgtgcggg     540
cccccgtcaa ttcctttgag tttcagtctt gcgaccgtac tccccaggcg gagtgcttaa     600
tgcgttagct gcagcactaa ggggcggaaa ccccctaaca cttagcactc atcgtttacg     660
gcgtggacta ccagggtatc taatcctgtt cgctccccac gctttcgctc ctcagcgtca     720
gttacagacc agagagtcgc cttcgccact ggtgttcctc cacatctcta cgcatttcac     780
cgctacacgt ggaattccac tctcctcttc tgcactcaag ttccccagtt ccaatgacc     840
ctccccggtt gagccggggg ctttcacatc agacttaaga aaccgcctgc gagccctta     900
cgcccaataa ttccggacaa cgcttgccac ctacgtatta ccgcggctgc tggcacgtag     960
ttagccgtgg ctttctggtt aggtaccgtc aaggtgccgc cctatttgaa cggcacttgt    1020
tcttccctaa caacagagct ttacgatccg aaaaccttca tcactcacgc ggcgttgctc    1080
cgtcagactt tcgtccattg cggaagattc cctactgctg cctcccgtag gagtctgggc    1140
cgtgtctcag tcccagtgtg gccgatcacc ctctcaggtc ggctacgcat cgtcgccttg    1200
gtgagccgtt acctcaccaa ctagctaatg cgccgcgggt ccatctgtaa gtggtagccg    1260
```

-continued

| | | | | |
|---|---|---|---|---|
| aagccacctt | ttatgtctga | accatgcggt | tcagacaacc | atccggtatt | agccccggtt | 1320 |
| tcccggagtt | atcccagtct | tacaggcagg | ttacccacgt | gttactcacc | cgtccgccgc | 1380 |
| taacatcagg | gagcaagctc | ccatctgtcc | gctcgacttg | ca | | 1422 |

<210> SEQ ID NO 5
<211> LENGTH: 1421
<212> TYPE: DNA
<213> ORGANISM: Bacillus amyloliquefaciens
<220> FEATURE:
<221> NAME/KEY: misc_feature
<222> LOCATION: (1405)..(1405)
<223> OTHER INFORMATION: n is a, c, g, or t

<400> SEQUENCE: 5

| | | | | | | |
|---|---|---|---|---|---|---|
| tgcagtcgag | cggacagatg | ggagcttgct | ccctgatgtt | agcggcggac | gggtgagtaa | 60 |
| cacgtgggta | acctgcctgt | aagactggga | taactccggg | aaaccggggc | taataccgga | 120 |
| tggttgtttg | aaccgcatgg | ttcagacata | aaaggtggct | tcggctacca | cttacagatg | 180 |
| gacccgcggc | gcattagcta | gttggtgagg | taacggctca | ccaaggcgac | gatgcgtagc | 240 |
| cgacctgaga | gggtgatcgg | ccacactggg | actgagacac | ggcccagact | cctacgggag | 300 |
| gcagcagtag | ggaatcttcc | gcaatggacg | aaagtctgac | ggagcaacgc | cgcgtgagtg | 360 |
| atgaaggttt | tcggatcgta | aagctctgtt | gttagggaag | aacaagtgcc | gttcaaatag | 420 |
| ggcggcacct | tgacggtacc | taaccagaaa | gccacggcta | actacgtgcc | agcagccgcg | 480 |
| gtaatacgta | ggtggcaagc | gttgtccgga | attattgggc | gtaaagggct | cgcaggcggt | 540 |
| ttcttaagtc | tgatgtgaaa | gcccccggct | caaccgggga | gggtcattgg | aaactgggga | 600 |
| acttgagtgc | agaagaggag | agtggaattc | cacgtgtagc | ggtgaaatgc | gtagagatgt | 660 |
| ggaggaacac | cagtggcgaa | ggcgactctc | tggtctgtaa | ctgacgctga | ggagcgaaag | 720 |
| cgtggggagc | gaacaggatt | agataccctg | gtagtccacg | ccgtaaacga | tgagtgctaa | 780 |
| gtgttagggg | gtttccgccc | cttagtgctg | cagctaacgc | attaagcact | ccgcctgggg | 840 |
| agtacggtcg | caagactgaa | actcaaagga | attgacgggg | gcccgcacaa | gcggtggagc | 900 |
| atgtggttta | attcgaagca | acgcgaagaa | ccttaccagg | tcttgacatc | ctctgacaat | 960 |
| cctagagata | ggacgtcccc | ttcggggggca | gagtgacagg | tggtgcatgg | ttgtcgtcag | 1020 |
| ctcgtgtcgt | gagatgttgg | gttaagtccc | gcaacgagcg | caacccttga | tcttagttgc | 1080 |
| cagcattcag | ttgggcactc | taaggtgact | gccggtgaca | aaccggagga | aggtggggat | 1140 |
| gacgtcaaat | catcatgccc | cttatgacct | gggctacaca | cgtgctacaa | tggacagaac | 1200 |
| aaagggcagc | gaaaccgcga | ggttaagcca | atcccacaaa | tctgttctca | gttcggatcg | 1260 |
| cagtctgcaa | ctcgactgcg | tgaagctgga | atcgctagta | atcgcggatc | agcatgccgc | 1320 |
| ggtgaatacg | ttcccgggcc | ttgtacacac | cgcccgtcac | accacgagag | tttgtaacac | 1380 |
| ccgaagtcgg | tgaggtaacc | tttanggagc | cagccgccga | a | | 1421 |

<210> SEQ ID NO 6
<211> LENGTH: 1421
<212> TYPE: DNA
<213> ORGANISM: Bacillus amyloliquefaciens
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (1417)..(1417)
<223> OTHER INFORMATION: n is a, c, g, or t -continued

```
<400> SEQUENCE: 6
tcggcggctg gctccntaaa ggttacctca ccgacttcgg gtgttacaaa ctctcgtggt      60
gtgacgggcg gtgtgtacaa ggcccgggaa cgtattcacc gcggcatgct gatccgcgat     120
tactagcgat tccagcttca cgcagtcgag ttgcagactg cgatccgaac tgagaacaga     180
tttgtgggat tggcttaacc tcgcggtttc gctgcccttt gttctgtcca ttgtagcacg     240
tgtgtagccc aggtcataag gggcatgatg atttgacgtc atccccacct tcctccggtt     300
tgtcaccggc agtcaccta gagtgcccaa ctgaatgctg gcaactaaga tcaaggttg      360 cgctcgttgc gggacttaac ccaacatctc acgacacgag ctgacgacaa ccatgcacca     420
cctgtcactc tgcccccgaa ggggacgtcc tatctctagg attgtcagag gatgtcaaga     480
cctggtaagg ttcttcgcgt tgcttcgaat taaaccacat gctccaccgc ttgtgcgggc     540
ccccgtcaat tcctttgagt ttcagtcttg cgaccgtact ccccaggcgg agtgcttaat     600
gcgttagctg cagcactaag gggcggaaac cccctaacac ttagcactca tcgtttacgg     660
cgtggactac cagggtatct aatcctgttc gctcccacg ctttcgctcc tcagcgtcag     720
ttacagacca gagagtcgcc ttcgccactg gtgttcctcc acatctctac gcatttcacc     780
gctacacgtg gaattccact ctcctcttct gcactcaagt tccccagttt ccaatgaccc     840
tccccggttg agccggggc tttcacatca gacttaagaa accgcctgcg agccctttac     900
gcccaataat tccggacaac gcttgccacc tacgtattac cgcggctgct ggcacgtagt     960
tagccgtggc tttctggtta ggtaccgtca aggtgccgcc ctatttgaac ggcacttgtt    1020
cttccctaac aacagagctt tacgatccga aaaccttcat cactcacgcg gcgttgctcc    1080
gtcagacttt cgtccattgc ggaagattcc ctactgctgc ctcccgtagg agtctgggcc    1140
gtgtctcagt cccagtgtgg ccgatcaccc tctcaggtcg gctacgcatc gtcgccttgg    1200
tgagccgtta cctcaccaac tagctaatgc gccgcgggtc catctgtaag tggtagccga    1260
agccaccttt tatgtctgaa ccatgcggtt cagacaacca tccggtatta gccccggttt    1320
cccggagtta tcccagtctt acaggcaggt tacccacgtg ttactcaccc gtccgccgct    1380
aacatcaggg agcaagctcc catctgtccg ctcgacntgc a                        1421
```